United States Patent [19]

Kirchhoff et al.

[11] Patent Number: 4,642,329

[45] Date of Patent: Feb. 10, 1987

[54] PREPOLYMER PROCESSING OF ARYLCYCLOBUTENE MONOMERIC COMPOSITIONS

[75] Inventors: Robert A. Kirchhoff; Alan Schrock; Jo A. Gilpin, all of Midland, Mich.

[73] Assignee: The Dow Chemical Company, Midland, Mich.

[21] Appl. No.: 770,913

[22] Filed: Aug. 30, 1985

Related U.S. Application Data

[63] Continuation-in-part of Ser. No. 644,836, Aug. 27, 1984.

[51] Int. Cl.$^4$ ............................................. C08F 32/00
[52] U.S. Cl. ................................. 526/284; 528/271; 528/298; 528/396
[58] Field of Search ............... 526/280, 284; 528/271, 528/298, 396

[56] References Cited

U.S. PATENT DOCUMENTS

| | | | |
|---|---|---|---|
| 2,917,499 | 12/1959 | Cripps | 564/281 |
| 3,366,616 | 1/1968 | Tietz | 526/308 |
| 3,470,137 | 9/1969 | Blanchard | 528/270 |
| 3,523,928 | 8/1970 | Blanchard | 528/270 |

OTHER PUBLICATIONS

*Chemical and Engineering News*—"Thermoset Resin Systems from AB Aromatic (Benzocyclobutene/Alkyne) Imide Monomers", Jul. 29, 1985.

*Chemical and Engineering News*—"New High-Temperature Thermoset Systems Based on Bio-Benzocyclobutene", Jul. 29, 1985.

*Primary Examiner*—Paul R. Michl

[57] ABSTRACT

Reactive polymeric compositions are prepared by subjecting arylcyclobutene monomeric compositions to polymerization conditions to provide a partially polymerized composition; and removing the partially polymerized composition from said conditions. The partially polymerized composition can be subsequently subjected to polymerization and curing conditions to provide a cured polymeric composition.

48 Claims, No Drawings

PREPOLYMER PROCESSING OF ARYLCYCLOBUTENE MONOMERIC COMPOSITIONS

CROSS-REFERENCE TO RELATED APPLICATION

This is a continuation-in-part of copending U.S. Application Ser. No. 644,836, filed on Aug. 27, 1984.

BACKGROUND OF THE INVENTION

This invention relates to a process for preparing polymeric compositions from arylcyclobutene monomeric compositions, and particularly to such a process using partially polymerized compositions of arylcyclobutene monomers.

Arylcyclobutene monomeric compositions are useful in preparing thermoset and thermoplastic polymeric compositions. Such polymeric compositions are highly desirable because they exhibit excellent thermal stability and chemical resistance. Such polymeric compositions typically can exhibit thermal degradation temperatures above 300° C., and are insoluble in many organic solvents and in water. Therefore, they find uses as films, coatings, adhesives, fiber-reinforced plastics, composites, structural laminates and other engineering applications.

Typically, arylcyclobutene monomeric compositions are provided in solid or powder form. One useful polymerization technique is to heat the monomeric composition to a sufficient polymerization temperature. Unfortunately, the melted monomers exhibit a low viscosity which decreases its effectiveness in processing. For example, when used as a coating, or an adhesive the low viscosity melted monomer can flow off of the intended surface or substrate. Also, for example, in compression molding processes, the low-viscosity melted monomer can leak out of the mold. Moreover, the polymeric compositions exhibit an undesirable amount of volumetric shrinkage when prepared directly from the monomeric compositions.

In view of the disadvantages of known methods, it would be desirable to provide reactive compositions from arylcyclobutene monomeric compositions which could be readily employed to prepare cured polymeric compositions in fabrication processes wherein the reactive compositions do not have an ineffectively low viscosity, and which substantially retain their volume upon curing. It is also desirable to have a process for preparing polymeric compositions from arylcyclobutene monomeric compositions which would not experience such difficulties.

SUMMARY OF THE INVENTION

This invention is a process for preparing reactive polymeric compositions from an arylcyclobutene monomeric composition. The process comprises (a) subjecting the monomeric composition to polymerization conditions to provide a partially polymerized composition; and (b) removing the partially polymerized composition from said conditions. The partially polymerized composition contains unreacted polymerization sites and can subsequently be subjected to polymerization and curing conditions to provide a cured polymeric composition.

The partially polymerized composition provided in the process of this invention is a reactive composition which can be employed to prepare cured polymeric compositions in fabrication processes, wherein the partially polymerized compositions do not have an ineffectively low viscosity, and substantially retain their volume upon curing. The partially polymerized compositions of this invention are substantially stable at room temperature.

As used herein, "reactive polymeric composition" refers to a composition which contains an amount of arylcyclobutene monomers in polymerized yet uncured form. Therefore, there exist unreacted polymerization sites in the polymeric composition.

This invention is useful in preparing polymeric compositions from arylcyclobutene monomeric compositions. Such polymeric compositions are useful in thermoset and thermoplastic resin applications, for example, as coatings, films, composites, fiber-reinforced plastics, structural laminates, adhesives, molded objects, and the like. The polymeric compositions exhibit physical properties which make them desirable for uses in many industries. For example, some polymeric compositions can have a dielectric constant below 3.5, dissipation factors lower than 0.004 at $10^3$ Hz, and thermal stability of greater than 400° C. which renders them useful in the electronics industry. The polymeric compositions are useful for forming electronic circuit boards, for encapsulating integrated circuits, as die attach materials, as planarization resins and as housings for electronic switches. The polymeric compositions are also useful in the automotive industry as valve covers, manifolds, distributor caps, water pumps and leaf springs. Yet another use is as microwave dishes. The reactive polymeric compositions can be employed as adhesives in many industries such as, for example, the aeronautical and aerospace industries.

DETAILED DESCRIPTION OF THE INVENTION

The monomeric compositions of this invention comprise an arylcyclobutene monomer. An arylcyclobutene monomer is a molecule which contains at least one, and preferably two or more arylcyclobutene moieties bonded thereto, such that under ring opening conditions, the cyclobutene ring can provide addition polymerization sites. Monomers containing one arylcyclobutene moiety are referred to hereinafter as mono-arylcyclobutene monomers. Monomers containing two or more moieties are referred to as poly(arylcyclobutene)monomers. Preferred mono-arylcyclobutene monomers contain an ethylenically unsaturated group, or other moiety which is reactive with an arylcyclobutene moiety. Preferred poly(arylcyclobutene)monomers will be described hereinafter. Typically, the arylcyclobutene moieties are pendantly bonded to the molecular composition. The monomeric composition can contain other compositions such as, for example, monomers copolymerizable with the arylcyclobutene monomers such as other monomers containing arylcyclobutene moieties, ethylenically unsaturated moieties, acetylenic moieties, and other compositions which can undergo addition polymerization reactions; miscible compositions, such as blowing agents, fire-retarding agents and the like; fillers such as glass fibers, quartz glass, powdered silica and the like; metal and ceramic powders for electrical conductive and insulative properties and the like.

The partially polymerized composition of this invention is a composition comprising an amount of the arylcyclobutene monomer in polymerized yet uncured form. Therefore, reactive polymerization sites remain on the monomer. The mixture comprising the partially polymerized form can also comprise an amount of completely unreacted monomer, an amount of oligomeric compositions, an amount of cured polymeric composition as well as an amount of the other compositions described above which are included in the monomeric composition.

An arylcyclobutene moiety is an aryl moiety to which one or more cyclobutene rings are fused. Aryl moieties are those referred to as aromatic compounds which contain $(4n+2)\pi$ electrons as described in Morrison and Boyd, *Organic Chemistry*, 3rd ed., 1973. Examples of suitable aryl moieties include benzene, napthalene, phenanthrene, anthracene, pyridine, a biaryl moiety, or 2 or more aromatic moieties bridged by alkylene or cycloalkylene moieties. Preferred aryl moieties are benzene, napthalene, biphenyl, binaphthyl, diphenyl alkane or diphenyl cycloalkane moieties. The more preferred aryl moiety is a benzene moiety.

Polymeric compositions are prepared from the arylcyclobutene monomeric composition by subjecting the monomeric composition to suitable polymerization conditions. Such conditions are those at which the cyclobutene ring opens to provide addition polymerization sites. Arylcyclobutene monomeric compositions can be polymerized by radiation, for example, by subjecting the composition to gamma-, electron beam, ultraviolet or thermal radiation. Thermal radiation is preferred because of its versatility, availability, and adaptability to a variety of systems.

The mono-arylcyclobutene monomers can correspond to the formula

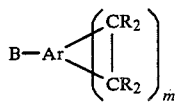

wherein B is a molecular composition corresponding to a bridging member of the poly(arylcyclobutene)monomers; Ar is an aryl moiety; R is separately in each occurrance hydrogen, or an electron-withdrawing substituent or an electron-donating substituent; and m is an integer of 1 or more.

The preferred mono-arylcyclobutene monomers, which contain an ethylenically unsaturated hydrocarbon moiety, or a moiety which is reactive with the cyclobutene ring of an arylcyclobutene moiety can correspond to the same formula, wherein B is a molecular composition containing such moieties. The substituents of the formula will be described further in the description of the poly(arylcyclobutene)monomers.

Preferably, the mono-arylcyclobutene monomers are mono-benzocyclobutene monomers, which can correspond to the formula

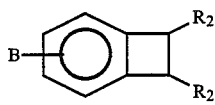

wherein B and R are described above. The molecular composition B can be bonded to any site on the aryl moiety; however, because of reaction considerations the meta-sites are preferred.

Preferred molecular compositions for B include structures corresponding to the formulae: $CH_2=CH-$,

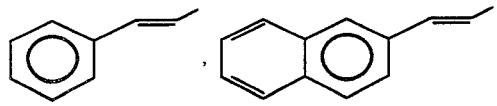

The mono- and poly(arylcyclobutene)monomers can be prepared in similar methods. The main differences in the preparations are that the mono-arylcyclobutene monomers are prepared from a molecular compound with only one reactive moiety while the poly(arylcyclobutenes) employ a compound with two or more reactive moieties; and at least two times the equivalent amount of arylcyclobutene compound is employed when preparing the poly(arylcyclobutene)monomers. Because, of their multiple reactivity provided by the multiple arylcyclobutene moieties, poly(arylcyclobutene)monomeric compositions are preferred.

The aryl moiety and cyclobutene ring can be substituted with a variety of substituents. Such substituents can be electron-donating or electron-withdrawing groups. Electron-donating groups are groups which, relative to hydrogen, can more readily donate an electron. Electron-withdrawing groups are groups which, relative to hydrogen, can more readily withdraw an electron. Examples of such substituents include cyano, halo, carboxy, hydrocarbyloxy, carbonyl, alkanoyl, aroyl, alkylsulfonyl, alkylsulfonoyl, amino, amido, or aryl groups.

The arylcyclobutene moieties are connected herein by a direct bond or bridging member. A bridging member (or molecular composition for the mono-arylcyclobutene monomers) is a single nuclear or molecular chain supporting the arylcyclobutene moieties. Suitable bridging members comprise (1) a polyvalent inorganic moiety, or (2) a polyvalent organic moiety which can contain (a) one or more heteroatoms, comprising O, P, N, or S, or (b) one or more aromatic moieties. The bridging member or direct bond connects the arylcyclobutene moieties through the aryl moiety.

Polyvalent inorganic moiety refers to any inorganic moiety which can bond to 2 or more aryl moieties. Such polyvalent inorganic moieties can be covalently or ionically bonded to the aromatic moiety. Examples of polyvalent inorganic moieties include oxygen, phosphorus, phosphorus oxide, sulfur, nitrogen, silicon, polysiloxanes, polyvalent metals, sulfoxide, sulfone, a polyvalent metal bound to a polyvalent oxygenated moiety wherein the polyvalent oxygenated moiety can be further bound to an aryl moiety (for example, a polyvalent carboxylate salt). Preferred polyvalent inorganic moieties include oxygen, sulfur, polysiloxanes, and polyvalent metals bound to polyvalent oxygenated moieties.

The polyvalent organic bridging member can be any polyvalent organic moiety bond to 2 or more aryl moieties. The organic bridging number can also contain one or more heteroatoms, comprising oxygen, nitrogen, phosphorus, or sulfur, or an organic moiety containing one or more aromatic moieties. Preferably, the polyvalent organic bridging member is a hydrocarbon poly-yl which is bonded to functionalized linking groups or a hydrocarbon poly-yl which contains an aromatic moiety. Hydrocarbon poly-yl is a hydrocarbon moiety which is bonded to 2 or more linking groups, wherein the hydrocarbon poly-yl can further contain one or more of the hereinbefore defined heteroatoms. Included within the term hydrocarbon are any organic moieties containing carbon and hydrogen atoms. Suitable hydrocarbons include the following organic moieties: alkanes, alkenes, alkynes, cycloalkanes, cycloalkenes, aromatic moieties, wherein aromatic is as defined hereinbefore, alkyl-substituted aromatic moieties, and aryl-substituted aliphatic moieties.

Linking group refers herein to any group which is capable of linking a hydrocarbon moiety to an aryl moiety. Linking groups include oxygen, sulfur, sulfoxide, sulfone, nitrogen, phosphorus, phosphorus oxide, oxycarbonyl, amido, carbonyl, carbonyldioxy, cyclic amido, carboxamidooxy, ureylene, carbonyloxycarbonyl, ammonium carboxylate salt and imido. Preferred linking groups are oxygen, sulfur, nitrogen, carbonyloxy, amido, carbonyldioxy, or cyclic amido. More preferred linking groups are carbonyloxy and amido.

Preferably the arylcyclobutene moieties are connected by direct bond or polyvalent organic moieties containing (1) one or more heteratoms or (2) one or more aromatic moieties or (3) an ethylenically unsaturated hydrocarbon moiety. Most preferably, the arylcyclobutene moieties are connected by the bridging members comprising the polyvalent organic moieties containing (1) one or more heteroatoms or (2) one or more aromatic moieties.

In one preferred embodiment, the polyvalent bridging member is a divalent bridging member. More preferred divalent bridging members include ethylenically unsaturated hydrocarbon moieties such as a vinyl moiety, dicarbonyloxy hydrocarbylene, dicarboxamido hydrocarbylene, dicarbonyldioxy hydrocarbylene, dioxyhydrocarbylene, dithiohydrocarbylene or an aromatic moiety-containing hydrocarbylene group.

Even more preferred divalent organic bridging members are dicarbonyloxyhydrocarbylene, dicarboxamidohydrocarbylene, di(carbonyloxy)hydrocarbylene, dioxyhydrocarbylene, and dithiohydrocarbylene.

Examples of polyvalent organic bridging members include the following: polyoxy(alk-poly-yl), polyoxy(ar-poly-yl), polyoxy(alkar-poly-yl), polyoxy(aralk-poly-yl), polythio(alk-poly-yl), polythio(ar-poly-yl), polythio(alkar-poly-yl), polythio(aralk-poly-yl), polyamido(alk-poly-yl), polyamido(ar-poly-yl), polyamido(alkar-poly-yl), polyamido(aralk-poly-yl), polycarbonyloxy(alk-poly-yl), polycarbonyloxy(ar-poly-yl), polycarbonyloxy(alkar-poly-yl), polycarbonyloxy(aralk-poly-yl), polycarbonyldioxy(alk-poly-yl), polycarbonyldioxy(ar-poly-yl), polycarbonyldioxy(alkar-poly-yl), polycarbonyldioxy(aralk-poly-yl), polyamino(alk-poly-yl), polyamino(ar-poly-yl), polyamino(alkar-poly-yl), polyamino(aralk-poly-yl), polycyclicimido(ar-poly-yl), polycyclicimido(alkar-poly-yl), polycyclicimido(aralk-poly-yl), polycarbonyl(alk-poly-yl), polycarbonyl(ar-poly-yl), polycarbonyl(alkar-poly-yl), polycarbonyl(aralk-poly-yl), polyimido(alk-poly-yl), polyimido(ar-poly-yl), polyimido(alkar-poly-yl), polyimido(aralk-poly-yl), polyureylene(alk-poly-yl), polyureylene(ar-poly-yl), polyureylene(alkar-poly-yl), polyureylene(aralk-poly-yl), polycarboxamideoxy(alk-poly-yl), polycarboxamideoxy(ar-poly-yl), polycarboxamideoxy(alkar-poly-yl), polycarboxamideoxy(aralk-poly-yl), ar-poly-yl, alkaryl-poly-yl, aralkyl-poly-yl, and alkenoic-poly-yl.

Hydrocarbyl means herein an organic moiety containing carbon and hydrogen atoms. The term hydrocarbyl includes the following organic moieties: alkyl, alkenyl, alkynyl, cycloalkyl, cycloalkenyl, aryl, aliphatic and cycloaliphatic aralkyl and alkaryl. Aliphatic refers herein to straight- and branched-, and saturated and unsaturated, hydrocarbon chains, that is, alkyl, alkenyl or alkynyl. Cycloaliphatic refers herein to saturated and unsaturated cyclic hydrocarbons, that is, cycloalkenyl and cycloalkyl. The term aryl refers herein to cyclic hydrocarbons containing $(4n+2)\pi$ electrons, such as biaryl, biphenylyl, phenyl, naphthyl, phenanthrenyl, anthracenyl and two aryl groups bridged by an alkylene group. Alkaryl refers herein to an alkyl-, alkenyl- or alkynyl-substituted aryl substituent wherein aryl is as defined hereinbefore. Aralkyl means herein an alkyl, alkenyl or alkynyl group substituted with an aryl group, wherein aryl is as defined hereinbefore. $C_{1-20}$ alkyl includes straight- and branched-chain methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl groups. $C_{1-5}$ alkyl includes methyl, ethyl, propyl, butyl and pentyl.

Cycloalkyl refers to alkyl groups containing one, two, three or more cyclic rings. Cycloalkenyl refers to mono-, di- and polycyclic groups containing one or more double bonds. Cycloalkenyl also refers to cycloalkenyl groups wherein two or more double bonds are present.

Hydrocarbylene refers herein to a divalent hydrocarbon moiety. Poly-yl refers herein to a polyvalent moiety, for example, ar-poly-yl refers to a polyvalent aromatic moiety. Poly refers herein to two or more.

Preferred arylcyclobutenes monomers (which include the mono-arylcyclobutene monomers described above) can correspond to the formula

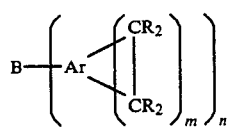

I wherein B is a direct bond or bridging member which comprises (1) a polyvalent inorganic moiety, or (2) a polyvalent organic moiety which can contain (a) one or more heteroatoms comprising oxygen, sulfur, nitrogen, or phosphorus, or (b) one or more aromatic moieties; Ar is an aromatic moiety which can be substituted; R is separately in each occurrence hydrogen or an electron-withdrawing or electron-donating substituent; m is an integer of 1 or more; and n is an integer of 1 or more, with the proviso that B can only be a direct bond wherein n is 2.

In one preferred embodiment, the aromatic moiety is benzene and m is 1. In this preferred embodiment, the arylcyclobutenes monomer can be referred to as a benzocyclobutene monomer. Preferred benzocyclobutene monomers can correspond to the formula

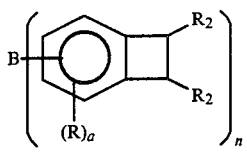
II wherein a is separately in each occurrence the integer 0, 1, 2, or 3; and B, R, and n are as defined hereinbefore. In formula II, a is preferably 0 or 1, and most preferably 0. R is preferably hydrogen, a cyano, or hydrocarbyloxycarbonyl group; more preferably hydrogen or cyano; and most preferably hydrogen.

In one embodiment, B can be a polyvalent inorganic bridging member, wherein inorganic bridging member is as defined hereinbefore. Preferable inorganic polyvalent moieties include —O—, —S—, —P—, —N—,

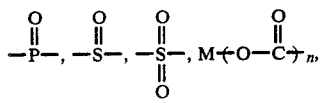

n valent M, or

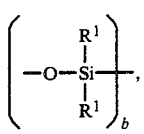

wherein M is a metal; $R^1$ is an alkyl, aryl, alkaryl, aralkyl, alkoxy, aryloxy, alkaryloxy or aralkyloxy; and b is an integer of 1 or greater. More preferable polyvalent inorganic bridging members include —O—, —S—, —N—,

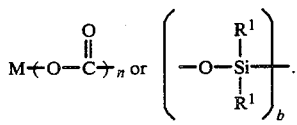

Polyvalent organic moiety is as defined hereinbefore. Preferred polyvalent organic moieties include those wherein B is (a) the formula X—(Z—)$_n$ wherein X is a hydrocarbon poly-yl moiety wherein the hydrocarbon poly-yl can contain a heteroatom of oxygen, phosphorus, sulfur or nitrogen, and Z is a functionalized linking moiety; or (b) a hydrocarbon poly-yl containing one or more aromatic moieties. Hydrocarbon poly-yl is as defined hereinbefore. The functionalized linking moiety is as defined hereinbefore. Preferably, X is an alk-poly-yl, cycloalk-poly-yl, ar-poly-yl, alkar-poly-yl, a biaromatic alkylene or cycloalkylene bridged poly-yl. More preferably, X is —(CH$_2$)$_p$—,

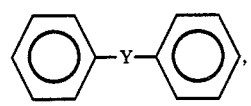

a phenylene, biphenylene, or cycloalkylene wherein Y is a C$_{1-20}$ straight- or branched-chain moiety or a cycloalkylene moiety and p is an integer of between about 2 and 20, inclusive. Most preferably X is —(CH$_2$)$_p$—, —CH=CH—, phenylene,

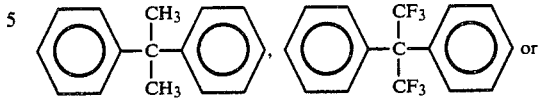

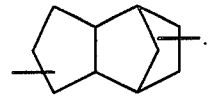

Preferably, Z is O, S, N, P,

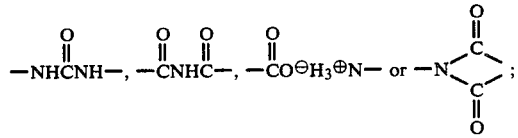

more preferably O, S,

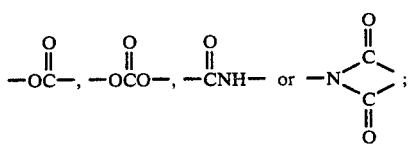

and most preferably

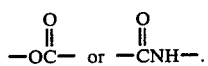

Preferred poly(benzocyclobutene) monomers include those with carboxamide-linking groups wherein the bridging members correspond to the formulae

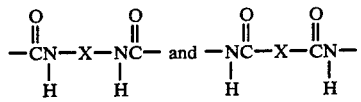

those with carbonyloxy-linking groups wherein the bridging members correspond to the formulae

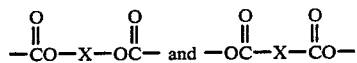

those with carbonyldioxy-linking groups wherein the bridging member corresponds to the formula

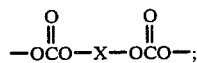

those with oxygen-linking groups wherein the bridging member corresponds to the formula

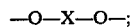

those with sulfur-linking groups wherein the bridging member corresponds to the formula

—S—X—S—;

and those with cyclic imide-linking groups wherein the bridging member corresponds to the formula

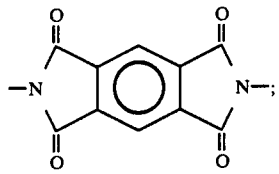

wherein X is as hereinbefore defined. More preferred bridging members which contain carboxamide-linking groups correspond to the following formulae:

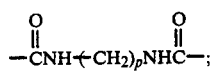

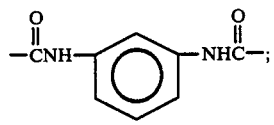

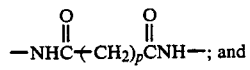

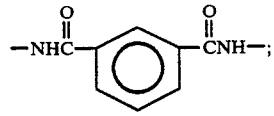

wherein p is as defined hereinbefore and p is an integer of 1 or greater, preferably between 1 and 20. More preferred bridging members with carbonyloxy-linking groups correspond to the formulae:

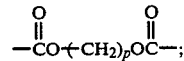

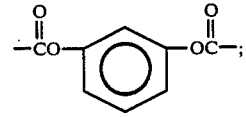

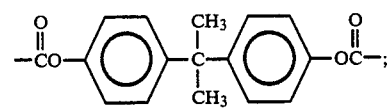

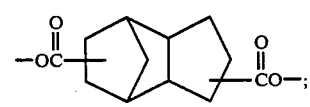

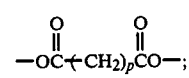

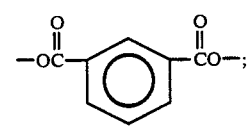

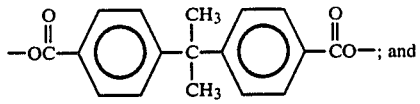

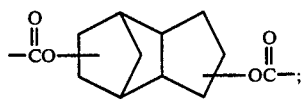

wherein p is as defined hereinbefore. Preferably, for photochemical polymerization processes, a benzophenone group is the bridging member. Such a group can correspond to the formula

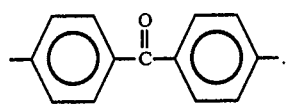

More preferred bridging members wherein the linking group is carbonyldioxy include those which correspond to the following formulae

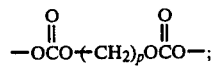

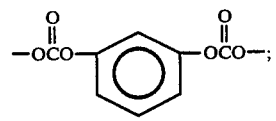

and

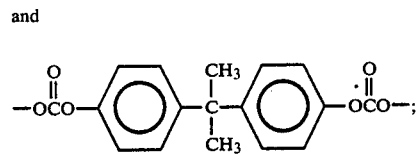

wherein p is as defined hereinbefore. More preferred bridging members with oxygen-linking groups include those which correspond to the formulae

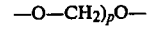

and

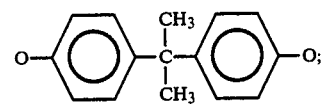

wherein p is as defined hereinbefore. More preferred bridging members with sulfur-linking groups include those which correspond to the formula

wherein p is as defined hereinbefore. More preferred bridging members with cyclic imid-linking groups include those which correspond to the formula

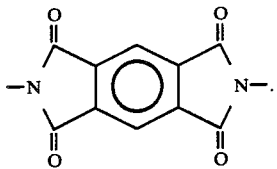

In one preferred embodiment, the polyvalent organic bridging member contains one or more aromatic moieties, and such bridging member generally corresponds to the formula

wherein Ar is as hereinbefore defined; $R^3$ is separately in each occurrence an alkylene, cycloalkylene or alkenylene radical; r is independently in each occurrence 0 or 1; and q is 1 or greater. $R^3$ is preferably a $C_{1\text{-}20}$ alkylene or $C_{1\text{-}20}$ alkenylene. $R^3$ is more preferably $C_{1\text{-}10}$ alkylene or $C_{1\text{-}10}$ alkenylene. $R^3$ is even more preferably $C_{1\text{-}4}$ alkylene or $C_{1\text{-}4}$ alkenylene, with —CH=CH— being most preferred. Preferably q is between 1 and 20, most preferably between 1 and 10. In a more preferred embodiment, the aromatic radical hydrocarbon poly-yl bridging member corresponds to the formula

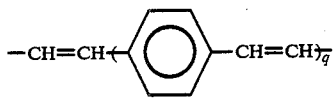

wherein q is as hereinbefore defined.

The arylcyclobutene monomers can be prepared by several synthesis schemes. The preferred methods of preparation of such monomers are described hereinafter.

In one synthesis scheme, an alkyl-substituted aromatic compound which is further substituted with an aryl deactivating substituent is chloroalkylated in a position ortho to the alkyl group. In the preferred embodiment wherein the aromatic compound is benzene, the starting material can correspond to the following formula

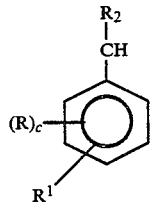

wherein R is as hereinbefore; $R^1$ is any aryl deactivating substituent; and c is an integer of 0, 1, 2, or 3. The alkyl-substituted aromatic compound can be chloroalkylated by contacting the alkyl aromatic compound with a chloroalkylating agent and thionyl chloride in the presence of an iron chloride catalyst to provide a product which contains a chloroalkyl group ortho to the alkyl substituent. In the embodiment wherein the aromatic compound is a benzene ring, the product can correspond to the formula

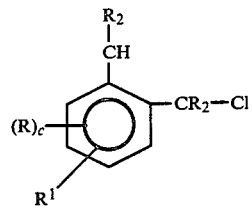

wherein R is as defined hereinbefore and $R^1$ is an aryl deactivating group. $R^1$ is preferably a hydrocarbyloxycarbonyl, carboxamide, hydrocarbylcarbonyl, carboxylate, halocarbonyl, nitrile, nitro, sulfone or sulfoxide group. $R^1$ is more preferably a halo or hydrocarbyloxycarbonyl group, with hydrocarbyloxycarbonyl being the most preferred group. Preferably c is 0 or 1, most preferably 0.

In this process the chloroalkylating agent is preferably chloromethyl ether, although other chloroalkylating agents such as bis(chloromethyl)ether could be used. At least a 2:1 molar excess of the chloroalkylating agent to the alkyl-substituted aromatic compound is needed. It is preferable to use at least about a 3:1 ratio of chloroalkylating agent to alkyl aromatic compound. The catalyst is ferric chloride ($FeCl_3$) which the cocatalyst is thionyl chloride. The catalyst can be present in between about 0.05 and 1.0 mole per mole of alkyl aromatic. More preferably between about 0.1 and 0.4 mole of catalyst are present for each mole of alkyl aromatic compound. Preferably between about 0.05 and 1.0 mole of thionyl chloride per mole of alkyl aromatic is used, more preferably between about 0.1 and 0.4 mole per mole of alkyl aromatic.

This process can be performed at a temperature of between about 40° C. and 80° C., preferably about 40° C. and 60° C. Below about 40° C., the reaction rate is low. The boiling point of some of the components of the reaction mixture starts at about 60° C.

This process can be performed by contacting the alkyl aromatic compound with the chloroalkylating agent, catalyst and cocatalyst in a suitable solvent. Suitable solvents are those solvents which are inert toward the chloroalkylating agent, and can include chlorinated hydrocarbon solvents. Thereafter the reaction mixture is heated to the appropriate temperature. The product can be recovered by quenching the reaction mixture with alcohols or water to inactivate the chloroalkylating agents remaining, stripping off the volatiles and washing out the catalyst with water. The product thereafter is recovered by distillation.

The ortho chloroalkylated alkyl aromatic compounds can be converted to aromatic compounds with cyclobutene rings fused thereto, by pyrolysis. This is achieved by contacting the ortho chloroalkylated alkyl aromatic compound with at least 2 times its weight of a suitable diluent, and thereafter passing the mixture through a reactor at a temperature of 550° C. or greater and a pressure of between about atmospheric and 25 mm of mercury. Suitable diluents are generally substituted aromatic compounds which are inert to the chloroalkylated alkyl aromatic compound and are stable at pyrolysis temperatures. Examples of suitable diluents are benzene, toluene, xylenes, chlorobenzenes, nitrobenzenes, methylbenzoates, phenyl acetate or diphenyl acetate. Preferred diluents are the xylenes. Preferable temperatures are between about 700° C. and 750° C.

Preferable pressures are between about 35 and 25 mm of mercury. In a preferred embodiment, the reaction mixture is passed through a hot tube packed with an inert material, for example, quartz chips or stainless steel helices. The product can be recovered by distillation. The product wherein the aromatic compound is benzene can correspond to the formula

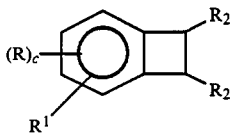

wherein R, $R^1$ and c are as hereinbefore defined.

In the preferred embodiment wherein $R^1$ is a hydrocarbyloxy carbonyl moiety, the hydrocarbyloxy carbonyl moiety can be converted to a carboxylate moiety by contacting the substituted (arylcyclobutene) compound with at least a molar equivalent of alkali metal hydroxide in an alkanol-water solvent system. In the embodiment wherein the aromatic moiety is benzene, the product can correspond to the formula

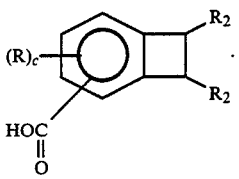

Thereafter the carboxylate-substituted (arylcyclobutene) compound can be converted to an acid chloride by contacting the carboxylate-substituted (arylcyclobutene) compound with thionyl chloride and refluxing at 70° C. to 80° C. The acid halide-substituted (arylcyclobutene) so formed can be used to prepare the monomers useful in this invention, as described hereinafter. In the embodiment wherein the aryl moiety is a benzene ring, the product corresponds to the formula

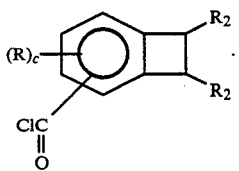

In an alternative synthesis, an aryl compound with ortho dibromomethyl groups can be converted to a 1,2-diiodoarylcyclobutene, by contacting the aryl compound substituted with ortho dibromomethyl moieties with an alkali metal iodide in an alkanol solvent at reflux so as to form the diiodoarylcyclobutenes. The product can be recovered by filtering, evaporating the filtrate and recrystallizing the product. In the embodiment wherein the aryl moiety is a benzene moiety, the starting material corresponds to the formula

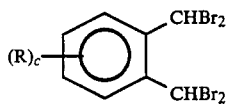

and the iodobenzocyclobutene can correspond to the formula

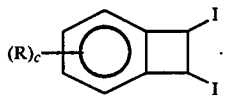

The 1,2-diiodoarylcyclobutenes can be converted to arylcyclobutenes by dissolving the 1,2-diiodoarylcyclobutenes in an alcohol solvent, preferably methanol or ethanol and contacting the solution with an alkali metal hydroxide in the presence of a palladium-on-carbon catalyst and $H_2$ gas at a temperature of 20° C. to 30° C. In general, at least between about 2 and 4 moles of alkali metal hydroxide per mole of 1,2-diiodoarylcyclobutene is used. Preferably, between about 50 and 200 psi of hydrogen gas is used. The arylcyclobutenes prepared in this manner can be recovered by distillation. In the embodiment wherein the aryl moiety is a benzene moiety, the product corresponds to the formula

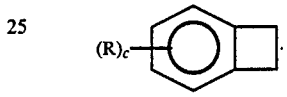

The arylcyclobutene can thereafter be brominated. In this process, the arylcyclobutene is dissolved in acetic acid and contacted with a brominating agent of pyridinium perbromide hydrobromide in the presence of mercuric salts, for example, mercuric acetate, at a temperature of between about 20° C. and 50° C. The brominated product can be recovered by extraction and distillation. In the embodiment wherein aryl moiety is benzene, the product corresponds to the formula

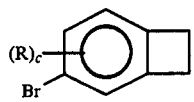

The brominated arylcyclobutene can thereafter be carbonylated to prepare a hydrocarbyloxy carbonyl-substituted arylcyclobutene. This carbonylation is achieved by dissolving the brominated arylcyclobutene in an alkanol solvent, and thereafter contacting the solution with carbon monoxide under pressure in the presence of a palladium catalyst, wherein the palladium is in the zero valence state, in the further presence of an acid acceptor under conditions such that the brominated arylcyclobutene compound undergoes carbonylation. Preferred catalysts are complexes prepared from palladium acetate and triphenyl phosphine, palladium triphenyl phosphine tetrakis, and bis(triphenyl phosphine)palladium chloride complex. The acid acceptor is generally a tertiary amine. In general, the reaction vessel is pressurized with carbon monoxide to a pressure of between atmospheric and 3000 psi, preferred pressures are between 600 and 1000 psi.

This process is preferably performed at a temperature of between 100° C. and 140° C., most preferably between 120° C. and 130° C. The hydrocarbyloxy carbonyl arylcyclobutene can be recovered by filtering off the catalysts, washing away the acid scavenger with a 10 percent strong mineral acid solution, stripping off the solvent and distilling. To prepare a carboxamide-substituted arylcyclobutene, a primary or secondary amine is substituted for the alcohol solvent. In the embodiment wherein the aryl moiety is a benzene moiety, the process corresponds to the following equation:

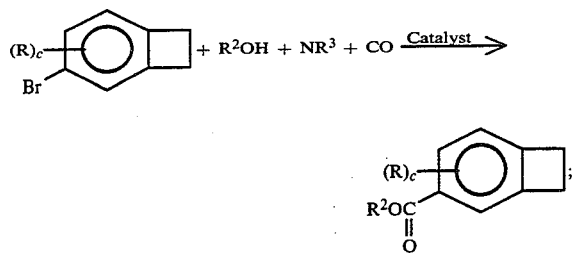

wherein R and c are as hereinbefore defined and $R^2$ and $R^3$ are hydrocarbyl moieties. The hydrocarbyloxy carbonyl-substituted or carboxamide-substituted arylcyclobutenes can thereafter be acidified and converted to acid chlorides by the process described hereinbefore.

The chlorocarbonyl-substituted arylcyclobutene compounds can be converted to arylcyclobutene monomers by contacting the halocarbonyl-substituted arylcyclobutene compounds with active hydrogen-containing compounds. Active hydrogen-containing compound refers herein to any compound which contains a hydrogen atom bonded to an oxygen, sulfur, phosphorus or nitrogen atom. For the purposes of this invention, an active hydrogen-containing compound refers to a compound containing a hydrogen atom which, because of its position in the molecule, displays significant activity according to the Zerewitnoff test described by Woller in the J. Am. Chem. Soc., 49, 3181 (1927). Illustrative of such active hydrogen moieties are —COOH, —OH, —NH$_2$, =NH, —CONH$_2$, —SH, and —CONH—. Such active hydrogen-containing compounds include polyols, polyamines, polyimides, polymercaptans, polyacids and the like. To prepare a arylcyclobutene monomer wherein the linking group is an amide, one contacts the halo carbonyl arylcyclobutene with an amine or polyamine. To prepare an arylcyclobutene monomer wherein the linking group is an imide, the active hydrogen-containing compound is an amide or polyamide. To prepare a arylcyclobutene monomer wherein the linking group is an ester, the active hydrogen-containing compound is an alcohol. To prepare an arylcyclobutene monomer wherein the linking group is an anhydride, the active hydrogen-containing compound is an acid. The active hydrogen-containing compounds useful in this invention generally correspond to the formula B—H)$_n$ wherein B and n are as hereinbefore defined. More preferably the active hydrogen-containing compound corresponds to the following formula X—Z—H)$_n$ wherein X, Z and n are as hereinbefore defined.

An alternative method to prepare an arylcyclobutene monomer with an amido- or polyamido(hydrocarbpoly-yl)-bridging member involves reacting an amino or polyamino hydrocarbon with at least one equivalent of a hydrocarbyloxy carbonyl arylcyclobutene for each amino moiety on the hydrocarbon. The reactants are dissolved in an equal volume of 1,2,4-trichlorobenzene and heated to 170° C. for about 6 hours. The alkanol by-product generated can be removed by distillation or absorption on a molecular sieve. The solvent is removed by washing it away with ethyl ether. The product prepared results in an amide-linking group wherein the nitrogen atom is bound to the carbonyl moiety.

Another preparation of an arylcyclobutene compound follows the reaction that reported by Skorcz and Kaminski, Org. Syn., 48, pages 53–56 (1968). In a typical preparation, an alkyl cyanoacetate is added to a solution of sodium metal in ethanol followed by the addition of an ortho-halomethylaryl halide. The alkyl 3-(O-haloaryl)-2-cyanopropionate is isolated and treated with aqueous sodium hydroxide. Subsequent acidification results in the cyanopropionic acid derivative. That derivative is placed into N,N-dimethylformamide and is refluxed to form the 3-(O-haloaryl)propionitrile derivative which is isolated and added to a suspension of sodamide in liquid ammonia. After an appropriate reaction time, ammonium nitrate is added and the ammonia allowed to evaporate. The cyanoarylcyclobutene is isolated by ether extraction and purified by fractional distillation under reduced pressure.

Substituted arylcyclobutenes can be prepared by the same technique by using the appropriately substituted reactants, such as an alkyl or alkoxybenzyl halide. Also substituents can result from using an alkyl haloacetate, alkyl acetoacetate or a dialkylmalonate.

In another preparation of an arylcyclobutene compound based on the paper by Matsura et al., Bull Chem. Soc. Jap., 39, 1342 (1966), o-aminoaryl carboxylic acid is dissolved in ethanol and hydrochloric acid added. Isoamylnitrite is slowly added to the cold stirred solution and diethyl ether is then added. The product, aryldiazonium-2-carboxylate hydrochloride, is filtered. That product is placed in a solvent, preferably ethylene dichloride, and acrylonitrile and propylene oxide is added to the stirred mixture which is then heated under nitrogen until the reaction is complete. After cooling, the mixture is filtered and the product, 1-cyanoarylcyclobutene, is isolated by fractionally distilling the filtrate under reduced pressure.

Amounts of reactants, reaction parameters and other details can be found in the cited article, the examples of this application, or can be easily deduced therefrom.

In a next sequence of reactions, the cyanoarylcyclobutene or substituted derivative is nuclear substituted. When the arylcyclobutene monomer to be prepared has an amide-linking group, the cyanoarylcyclobutene is aminated. In one preparation, the cyanoarylcyclobutene is added slowly to a cold solution of sodium nitrate in concentrated sulfuric acid to form 5-nitro-1-cyanoarylcyclobutene. That nitro compound is isolated, dissolved in ethanol and reduced by hydrogenation over a palladium on carbon catalyst. The isolated product is 5-amino-1-cyanoarylcyclobutene. In the preferred embodiment where the aryl moiety is benzene, the product corresponds to the formula

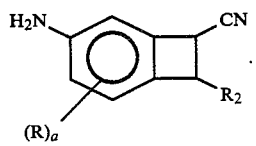

In another method of preparing the arylcyclobutene monomers, the amino-substituted arylcyclobutene is reacted with an appropriate coupling material. Coupling material refers herein to a compound which reacts with the amino or other substituent on the arylcyclobutene so as to form a bridging member with the amino or other substituent. Such processes are described hereinafter. In the embodiment wherein the bridging member contains amide-linking groups, the amino-substituted arylcyclobutenes are reacted with a polyvalent acid chloride. In practice, the amine-substituted arylcyclobutene is dissolved in a chlorinated aliphatic hydrocarbon solvent to which is added a tertiary amine, the acid acceptor, and thereafter the polyvalent acid chloride in a chlorinated aliphatic hydrocarbon solvent is added slowly to the mixture. This is preferably done at about 0° C. in an inert atmosphere. It is preferred to stir the reaction mixture for a period of time at 0° C. after the addition is complete.

To prepare a hydroxy-substituted arylcyclobutene, an amine-substituted arylcyclobutene is contacted with an alkali metal nitrite in the presence of aqueous sulfuric acid at 0° C., and thereafter the reaction mixture is heated to 100° C.

To prepare a mercapto-substituted arylcyclobutene, first an arylcyclobutene is reacted with chlorosulfonic acid to prepare an arylcyclobutene sulfonyl chloride. Arylcyclobutenyl sulfonyl chloride is reacted with zinc to prepare a mercapto-substituted arylcyclobutene. Alternatively, the arylcyclobutene is treated with a mixture of sulfur trioxide and dioxane at 0° C. followed by treatment with water. The arylcyclobutene-sulfonic acid is isolated and treated with phosphorous pentachloride to form the arylcyclobutene sulfonyl chloride which is then reduced with zinc to the mercapto-substituted arylcyclobutene.

An iodo-substituted arylcyclobutene can be prepared by reacting an amino-substituted arylcyclobutene with an alkali metal nitrite, sulfuric acid and potassium iodide at 0° C. under conditions such that an iodoarylcyclobutene is prepared.

An alkenyl-substituted arylcyclobutene can be prepared by reacting a bromo-substituted arylcyclobutene with an alkene, wherein the alkene contains a terminal olefin, in an aliphatic hydrocarbon solvent in the presence of a palladium catalyst such as palladium acetate, and a tertiary amine such as triethylamine. It is advantageous to use a slight excess of the bromo-substituted arylcyclobutene. The tertiary amine, which functions as an acid acceptor, is used in equimolar amounts with the bromo-substituted arylcyclobutene. The palladium catalyst is used in catalytically effective amounts. Generally this process can be performed at temperatures of between about 40° C. and 140° C.

To prepare an arylcyclobutene monomer with an alkene-poly-yl or alkenar-poly-yl-bridging member, an alkene or alkene-substituted aromatic compound which contains at least one terminal olefinic moiety is reacted with at least one mole of a bromo-substituted arylcyclobutene for each terminal olefin under conditions described hereinbefore.

To prepare an arylcyclobutene monomer in which the bridging member contains an amine-linking group, the amine-substituted arylcyclobutene is reacted with a compound which contains at least one alkyl halide moiety. In order to prepare an arylcyclobutene monomer in which the bridging member contains a linking group which is ureylene, the amine-substituted arylcyclobutene is reacted with a compound which contains at least one isocyanate or phosgene moiety.

To prepare an arylcyclobutene monomer in which the bridging member contains a linking group of a cyclic imide, the amine-substituted arylcyclobutene is reacted with a compound which contains at least one anhydride moiety.

To prepare an arylcyclobutene monomer with a polyvalent organic bridging member containing carbonyl-linking groups, the arylcyclobutene is reacted with an acid chloride with at least one acid chloride moieties, in the presence of aluminum chloride.

To prepare an arylcyclobutene monomer with a polyvalent organic bridging member containing an ammonium carboxylate-linking group, a carboxylate-substituted arylcyclobutene is contacted with a compound containing at least one polyamine-substituted moiety.

To prepare an arylcyclobutene monomer with a polyvalent organic bridging member containing thio-linking groups, a mercapto-substituted arylcyclobutene is reacted with an alkali metal hydroxide to prepare an alkali metal salt of the mercapto-substituted arylcyclobutene. The salt is then reacted with an organic compound containing at least one halo moiety to prepare an arylcyclobutene monomer with an organic bridging member containing thio-linking groups.

To prepare an arylcyclobutene monomer with a polyvalent organic bridging member containing nitrogen (amino)-linking groups, at least one equivalent of an amino-substituted arylcyclobutene are reacted with an organic compound containing at least one aldehyde moiety in the presence of an alkali metal cyanoborohydride under conditions that an arylcyclobutene monomer with a polyvalent organic bridging member with amino-linking moieties is prepared. One equivalent of amino-substituted arylcyclobutene for each aldehyde moiety on the organic aldehyde-containing compound is used. Alternatively, at least one equivalent of amine-substituted arylcyclobutene are reacted with an organic compound containing at least one bromo moiety in the presence of an alkaline earth metal carbonate under conditions such that an arylcyclobutene monomer with an organic bridging member containing amino-linking moieties is prepared. An equivalent of amino-substituted arylcyclobutene is used for each bromo moiety on the bromo-substituted organic compound.

To prepare arylcyclobutene monomers with polyvalent organic bridging members containing oxygen-linking moieties, a hydroxy-substituted arylcyclobutene is contacted with an alkali metal hydroxide to prepare an alkali metal salt of a hydroxy-substituted arylcyclobutene. At least one equivalent of the salt is then reacted with an organic compound containing at least one bromo moieties, under conditions such that an arylcyclobutene monomer with an organic bridging member containing oxygen-linking groups is prepared. One equivalent of the salt for each bromo moiety on the organic compound is used.

An alternative method of preparing the arylcyclobutene monomers wherein a carbonyl group is attached to the aryl moiety involves contacting the carboxylate-substituted arylcyclobutenes with 1',1-carbonyl-diimidazole in an ether solvent at 0° C. The reaction mixture is then heated until it reaches the reflux of the solvent and thereafter any active hydrogen-containing compound is added so as to prepare a arylcyclobutene monomer, wherein the bridging member contains a carbonyl group which is bonded to the aryl group of the arylcyclobutene.

In order to prepare a polysiloxane bridging member, the amino-substituted arylcyclobutene is reacted with a polychlorinated polysiloxane. Alternatively, a halocarbonyl-substituted arylcyclobutene is reacted with an aminoalkylterminated polysiloxane.

To prepare an arylcyclobutene monomer with a polyvalent inorganic bridging member comprising a carbonyl moiety, an acid-halide-substituted (arylcyclobutene) is reacted with an arylcyclobutene in the presence of $AlCl_3$ or $SnCl_4$.

To prepare an arylcyclobutene monomer with a carbonyldioxy inorganic bridging member, at least one and preferably two moles of a hydroxy-substituted arylcyclobutene is reacted with phosgene in the presence of a tertiary amine. To prepare an arylcyclobutene monomer with a bridging member of a polyvalent metal ionically bonded to a polyvalent carboxylate moiety, a carboxylate-substituted arylcyclobutene is reacted with a metal hydroxide to prepare a metal poly(arylcyclobutene)carboxylate. In general, the metal hydroxide is reacted with the number of moles of carboxylate-substituted arylcyclobutenes equal to the metal's coordination number. An arylcyclobutene monomer with a polyvalent metal bridging member is prepared by first reacting one equivalent of a bromine-substituted arylcyclobutene with one equivalent of magnesium in an ether solvent to prepare an arylcyclobutenyl magnesium bromide. To prepare a di(arylcyclobutenyl)magnesium, one equivalent of a brominated arylcyclobutene is reacted with one equivalent of magnesium. The arylcyclobutenyl magnesium bromide is reacted with a metal chloride to prepare an arylcyclobutenyl metal. The metal chloride is reacted with the number of equivalents of arylcyclobutenyl magnesium bromide equal to the metal's oxidation state.

To prepare an arylcyclobutene monomer with an inorganic bridging member of sulfur, a mercapto-substituted benzocyclobutene is reacted with an iodo-substituted arylcyclobutene in an amide solvent in the presence of an alkali metal hydroxide. Alternatively, the mercapto-substituted arylcyclobutene can be reacted with cuprous chloride to prepare a cuprous salt of a mercapto-substituted arylcyclobutene. The salt can thereafter be reacted with an iodo-substituted cyclobutene in an amide solvent to prepare an arylcyclobutene monomer with a sulfide bridging member. The sulfide bridging member can be converted to a sulfoxide by contacting the arylcyclobutene sulfide with one equivalent of peracetic acid under conditions to oxidize the sulfide to a sulfoxide. Alternatively, the sulfide can be converted to a sulfone by contacting the arylcyclobutene with at least two equivalent of peracetic acid under conditions to oxidize the sulfide to a sulfone.

To prepare an arylcyclobutene monomer with a phosphorus bridging member, an arylcyclobutene magnesium bromide is reacted with phosphorus trichloride to prepare a tri(arylcyclobutenyl)phosphine. The tri(arylcyclobutenyl)phosphine can be contacted with peracetic acid, so as to prepare a tri(arylcyclobutenyl)phosphine oxide.

To prepare an arylcyclobutene monomer with a nitrogen bridging member, an amino-substituted arylcyclobutene is reacted with a potassium hydride to prepare a potassium salt of an amine-substituted arylcyclobutene. The salt is then reacted with an iodoarylcyclobutene in liquid ammonia under ultraviolet light, under conditions that an arylcyclobutene with a nitrogen bridging member is prepared.

To prepare an arylcyclobutene monomer with an oxygen bridging member, at least one, and preferably two, equivalents of a hydroxy-substituted arylcyclobutene are reacted with cupric carbonate to prepare cupric salt comprising a copper cation and two anions of hydroxyarylcyclobutenes from which the hydroxyl hydrogens have been abstracted. The salt is then reacted with an iodoarylcyclobutene, at between 100° C. and 180° C., either neat or in an amide solvent, under conditions such that a di(arylcyclobutene)ether is prepared.

The arylcyclobutene monomeric compositions are useful in preparing polymeric compositions. In general, polymeric compositions can be prepared by subjecting the monomeric compositions to polymerization conditions. Typically, such conditions can include subjecting the monomeric compositions to radiation such as, for example, gamma-, electron-beam, ultraviolet, and thermal radiation. Thermal radiation is preferred because of its ready application. As described above, an arylcyclobutene polymeric composition comprises an arylcyclobutene monomer in polymerized form. The arylcyclobutene monomer can be a mono- or a poly(arylcyclobutene)monomer. The polymeric composition can also contain copolymerized monomers, and other compositions such as, for example, fillers, miscible compositions and the like. The arylcyclobutene monomeric composition can be polymerized by heating to the polymerization temperature of the particular monomer(s) used. The polymerization is an addition polymerization wherein no volatiles are generated. Furthermore, no catalyst initiator or curing agents are necessary for the polymerization to take place. However, in some cases employing a metal catalyst composition can lower the polymerization and cure temperature. Suitable compositions include copper catalysts and the like. It is believed that the polymerization takes place when the cyclobutene ring undergoes transformation to prepare a molecule resembling a 1,3-cyclohexadienyl moiety with two exo-olefinic unsaturated moieties adjacent to one another wherein each of the olefinic unsaturated moieties undergoes reaction with the olefinic unsaturated moieties of other 1,3-cyclohexadienyl-containing molecules which have undergone the same transformation as well as other moieties which undergo addition polymerization reactions. The temperature at which the arylcyclobutene monomers undergo polymerization is affected by the nature of any substituent on the cyclobutene ring. In some embodiments, the temperature of polymerization is as low as about 30° C. In preferred embodiments, the temperature at which polymerization is initiated is above 150° C., more preferably above about 200° C. It is to be noted that the temperature at which polymerization is initiated is dependent upon the nature of substituents on the cyclobutene ring. In general, wherein the cyclobutene ring is unsubstituted, the polymerization is initiated at about 200° C. Wherein the cyclobutene ring is substituted with an electron-donating substituent, the polymerization temperature is generally lowered, the higher the ability of the substituent to donate electrons, the lower the polymerization initiation temperature is. Conversely, the electron-withdrawing substituents on the cyclobutene ring result in higher polymerization initiation temperatures.

The unsubstituted cyclobutene in general polymerizes at the highest temperature.

It is believed the polymeric compositions prepared from the arylcyclobutenes monomeric compositions comprise units which can correspond to the formulae

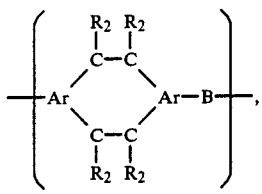

A and

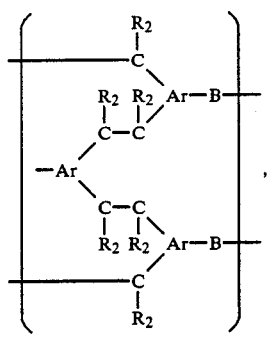

B and mixtures thereof. It is believed that the preferred polymeric compositions prepared from the arylcyclobutenes monomeric composition comprise mixtures of formulae A and B.

In those embodiments wherein Ar is benzene, it is believed that the polymeric compositions prepared from benzocyclobutene monomeric compositions comprise units which can correspond to the formulae

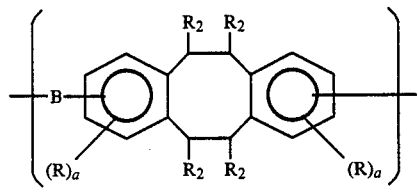

C and

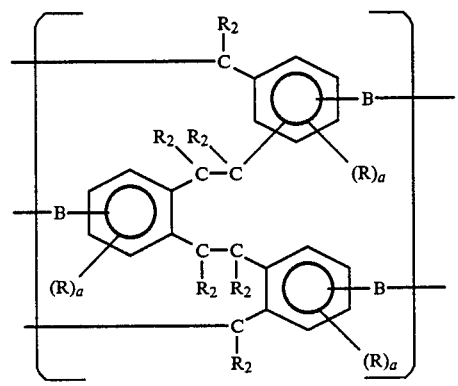

D and mixtures thereof. It is believed the preferred polymer compositions prepared comprise mixtures of formulae C and D with D being predominant.

The method of polymerization of the arylcyclobutene monomeric composition has a significant effect on the nature and properties of the polymeric composition prepared. In one embodiment, the arylcyclobutene monomeric compositions of this invention can be melt polymerized. The melt polymerization of arylcyclobutene monomeric compositions is useful to prepare solid parts, coatings, composites, adhesives and fibers.

In one embodiment of the melt polymerization, the monomeric composition can be heated above its melting temperature to provide a molten liquid. Such a temperature typically can range between about 80° C. and 200° C. The liquid can thereafter be poured or injected into a mold. Advantageously, pressure can be applied on the melted monomeric composition in the mold. Generally, pressures of between about 100 and 2000 psi are suitable. Thereafter, the monomeric composition can be heated to a temperature and time sufficient to polymerize and cure the composition. Such a temperature typically can range between about 200° C. and 300° C., preferably between about 200° C. and 250° C. and the time typically can range between about 10 minutes and 3 hours. Upon cooling, the polymeric composition can be removed from the mold.

Polymeric compositions prepared in this manner can subsequently be thermally treated at temperatures above 200° C. to raise the modulus and lower the coefficient of expansion of such polymeric compositions.

In general, the polymeric compositions prepared by this method are insoluble in many organic and aqueous solvents. They can swell but do not dissolve, are thermally stable at 200° C., have a good modulus, a low water pickup and are reasonably hard.

Suitable fillers and reinforcing materials can be, generally, in any powder form and/or fibrous products, for example, of the type commonly used in the production of moldings based on unsaturated polyester resins or epoxide resins. Examples of products such as these are, primarily, granular fillers such as quartz powder, ground shale, asbestos powder, powdered carborundum, chalk, iron powder, aluminum powder, sand, gravel and other fillers of this kind, also inorganic or organic fibers, more especially glass fibers in the usual textile forms of fibers, filaments rovings, yars, nonwovens, mats and cloths, etc. In this connection, amino silane-based finishes have proven to be particularly effective. It is also possible to use corresponding textile structures of organic, preferably synthetic fibers (polyamides, polyesters) or on the basis of quartz, carbon, metals, etc., as well as monocrystals (whiskers).

The monomeric compositions can be combined with fillers or reinforcing materials for use in particular in vessel and pipe construction by the winding technique, in electrical engineering, in mold construction and tool making and also in the construction of heavily stressed components, in the lightweight construction of vehicles in aeronautical and astronautical engineering.

In another embodiment, the arylcyclobutene monomeric compositions can be used to prepare coatings and films. In one embodiment, the monomeric composition can be dissolved in a suitable solvent and coated onto the substrate of choice. Thereafter the coated substrate is treated at temperatures of above the polymerization temperature of the monomeric composition. Preferably, the polymerization temperature is 150° C. or above, more preferably 200° C. or above. The coated substance is subjected to polymerization temperatures for a sufficient time for the polymerization to be completed. Preferably, such exposure times are between 10 minutes and 10 hours. Suitable solvents are those which volatilize away at temperatures below the polymerization temperature. Preferred solvents are cyclic and aliphatic ethers, lower alkanols, amides, and chlorinated hydrocarbon solvents. It is preferable to saturate the solvent with the monomeric composition, a 20 to 30 weight percent concentration of monomeric composition in the solvent is more preferred.

The arylcyclobutene monomeric compositions can be combined with the powder-form or fibrous fillers or reinforcing materials either before or after partially polymerizing the monomeric composition. For example, it is possible to impregnate powder-form or fibrous fillers or reinforcing materials such as quartz sand or glass cloths, with the arylcyclobutene monomeric compositions, optionally in solution.

In another embodiment, a film can be prepared from the arylcyclobutene monomeric compositions by powder coating techniques. In particular, the monomeric composition in a powder form can be placed on a desired substrate. Thereafter, the monomeric composition can be heated to its melt temperature over a time sufficient to melt the monomeric composition and allow the melted monomeric composition to form a liquid coating on the substrate. Thereafter, the melted monomeric composition coated on the substrate can be subjected to temperatures at which the monomeric composition polymerizes for a time sufficient for the monomeric composition to form a polymeric film on the desired substrate.

In another embodiment, the arylcyclobutene monomeric composition can be polymerized by solution polymerization techniques. In this embodiment, the monomeric composition can be dissolved in dipolar aprotic solvents with boiling points above the polymerization temperature of the monomeric composition. It is preferable that the solvents have a boiling point of near or above 200° C. and more preferable that the solvents have a boiling point of above 250° C. Examples of preferred dipolar aprotic solvents include amides and sulfones. It is necessary to add to the solution lithium salts which solubilize the polymeric composition in the solvents, preferably, between about 5 and 20 weight percent based on the solvent weight. A preferred lithium salt is lithium chloride. The polymerization takes place by heating the polymerization solution to a temperature at which the monomeric composition undergoes polymerization, preferably about 200° C. The polymerization time is preferably between about 1 and 10 hours. A partially polymerized composition can be formed in that time period, which can be removed from such conditions. The polymeric composition can be recovered by adding water to precipitate the polymeric composition from the reaction solution and thereafter stripping off the solvent. The polymeric composition prepared with this method can be used in compression moldings or to prepare coatings.

In another embodiment, the arylcyclobutene monomeric composition which undergo polymerization at a temperature which is below the melting point of the monomeric composition can be polymerized in a solid state polymerization. In this method, the monomeric composition is heated to a temperature at which polymerization takes place. A partially polymerized composition in this embodiment can be in a solid form. According to the process of this invention, after heating the monomeric compositions to the polymerization temperature, the composition is removed from the conditions after an amount of the monomer has polymerized. Polymeric compositions prepared in this method can be useful in the preparation of bearings, seals and other parts by powder metallurgy techniques.

In one embodiment of this invention, an amount of the arylcyclobutene monomeric composition is provided to a reaction vessel. The composition is subjected to heat to a temperature sufficient to initiate polymerization. Typically, the monomeric composition will melt before it polymerizes. The melting temperature can vary, and typically ranges from about 50° C. to about 250° C. The melted monomeric composition has a visibly low viscosity. As polymerization is initiated, the monomeric composition reaction mixture becomes visibly more viscous. The temperature at which polymerization is initiated can be determined by differential scanning calorimetry, and typically ranges from about 200° C. to about 300° C. The reaction mixture is removed from the heat after it forms a sufficiently viscous liquid mixture or gel. A sufficiently viscous mixture is one which has an effective viscosity. An "effective viscosity" is a viscosity which is greater than the initial viscosity of the melted monomer and which enables the partially polymerized composition to be used in processes without experiencing the difficulties of the low viscosity melted monomer. The effective viscosity can vary according to the particular process in which the partially polymerized composition is employed. The effective viscosity is at least about 10 percent greater, preferably at least 100 times greater, more preferably at last 1,000 times greater, and most preferably at least 10,000 times greater than the initial viscosity of the melted monomer, although any viscosity which renders the compositions useful for the particular purpose is suitable.

The partially polymerized composition liquid mixture can be cooled to provide a solid or a viscous liquid at room temperature. Upon subsequent heating, the solid can melt and return to the higher viscosity liquid. If the monomeric composition is incompletely heated, an insufficient viscosity can be obtained. If the monomeric composition is subjected to overheating a hard insoluble polymeric composition can be formed which is difficult to grind and fabricate as desired.

In another embodiment of this invention, an arylcyclobutene monomeric composition is mixed with a liquid composition which is a solvent for the monomeric composition, but which is a nonsolvent for the partially polymerized composition. A solvent for the monomeric composition is a liquid in which the individual molecules of the arylcyclobutene monomer can be dispersed throughout the molecules of the liquid. A nonsolvent for the partially polymerized composition is a liquid in which the molecules of the arylcyclobutene monomers in partially polymerized from coagulate and become insoluble. The mixture is subjected to sufficient polymerization conditions. As the partially polymerized composition forms it can precipitate out of the liquid and be collected. Advantageously, substantially all of the monomeric composition will form solvent-insoluble partially polymerized composition, yet not all of the polymerization sites will be reacted. Therefore, the precipitate can be collected, and subjected to further polymerization conditions to provide a cured polymeric composition.

The partially polymerized compositions of this invention can be employed in conventional fabrication processes to provide a cured polymeric composition. For example, the viscous reaction mixture can be placed in a compression molding device, and subjected to suitable temperature and pressure conditions to provide the cured polymeric composition. Surprisingly, when employing such a technique the cured polymeric composition exhibits substantially decreased volumetric shrinkage. The volume of the cured polymeric composition is greater than about 90 percent and preferably greater than about 95 percent of the volume of the partially polymerized composition.

The viscous partially polymerized composition can be employed as a coating wherein an effective amount of the neat partially polymerized composition as provided to a surface, and subsequently thermal treated to cure the composition. Further, the partially polymerized composition can be mixed with a suitable solvent. The solution can then be applied to a surface, the solvent evaporated, and the partially polymerized composition cured to provide a film. Yet another useful application for the viscous partially polymerized composition is in a reaction injection molding process or transfer molding. The viscous composition is injected into a mold, and then subjected to suitable temperature and pressure to cure the partially polymerized composition.

The second embodiment of this invention provides a partially polymerized composition in solid form which can be indefinitely stable at room temperature and ordinary conditions of pressure and humidity. The solid form can be readily ground to provide a powder. The powder can then be employed as a coating, a film, an adhesive and in temperature and pressure fabricating techniques. The partially polymerized compositions prepared in the precipitation method can exhibit a melting temperature.

It is desirable to employ the partially polymerized compositions in all uses of the arylcyclobutene monomeric compositions. For example, the partially polymerized composition is useful in adhesive uses, such as in preparing die attach materials, wherein a metal powder is employed along with the arylcyclobutene monomer. The viscous partially polymerized composition more effectively suspends and disperses the powder. The partially polymerized composition is also useful in preparing fibers. The viscous composition can be more effectively drawn into fibers than the low viscosity melted monomer. Further, the viscous partially polymerized composition is more effectively retained in pressure molding processes, such as in compression molding and reaction injection molding.

The following examples are provided to illustrate the invention and not to limit the scope of it.

PREPARATION OF ARYLCYCLOBUTENE COMPOUNDS

A. Preparation of 4-Carbomethoxybenzocyclobutene

A solution of methyl para-toluate (30 g, 0.20 mole) in 1,2-dichloroethane (80 ml) is added to a flask equipped with ice bath, stirrer, water-cooled condenser, ice traps and scrubber. To the stirred solution is added chloromethyl methyl ether (48 ml, 0.63 mole), thionyl chloride (5.8 ml, 0.080 mole), and last ferric chloride (6.5 g, 0.040 mole) in two portions. The cooling bath is removed, and the stirred reaction mixture is heated at 60° C. (heating lamp, controller) for 3 hours.

Methanol (150 ml) is added gradually to the cooled reaction mixture (exotherm). Low boiling components are removed under vacuum. The solution of product in dichloroethane is washed with water, 5 percent sodium bicarbonate solution, dried over anhydrous magnesium sulfate, filtered, and solvent is removed under vacuum. The product contains 13 percent unreacted methyl para-toluate and 80 percent methyl 3-chloromethyl-4-methylbenzoate (CMMT-chloromethylated methyl toluate) as analyzed by capillary gas chromatography. Recovery of the starting material by vacuum distillation affords a distillation residue of 91 percent pure product (analysis by capillary gas chromatography).

The pyrolysis unit is a quartz tube packed with quartz chips. The central portion of the tube is placed in a furnace. A 25-centimeter portion of the tube above the furnace serves as a preheating zone and the temperature in the middle of such preheating zone is between about 250° C. and 300° C. Attached to the top of the tube is an addition funnel. Attached to the bottom portion of the tube are cold traps and a means for pulling a vacuum on the tube. Methyl(3-chloromethyl)para-toluate (50 g) is dissolved in 200 g of ortho-xylene and placed in the addition funnel. The furnace is heated up to 730° C. A vacuum pump is turned on and pressure is adjusted to 25 ml of mercury. The solution of methyl(3-chloromethyl)para-toluate is added dropwise over a period of 1 hour and 15 minutes. Product and unreacted starting material are collected in cold traps. The pyrolytic tube is flushed with 200 ml of acetone after a cooling down period. The acetone solution is combined with the ortho-xylene solution collected in the cold traps. Acetone and ortho-xylene are distilled off with a 16-inch Vigreaux column under normal pressure. When most of the ortho-xylene is distilled, the system is brought to 0.02 mm mercury and 15.5 g of pure 4-carbomethoxybenzocyclobutene is collected at 61° C. The residue left in the distillation pot is methyl(3-chloromethyl)-para-toluate, 23 g.

B. Preparation of 1-Cyanobenzocyclobutene

A mixture of benzenediazonium-2-carboxylate hydrochloride (1.92 g), acrylonitrile (0.80 g) and propylene oxide (0.58 g) in 100 ml of ethylene dichloride is stirred in a flask under nitrogen at 50°-60° C. for 4 hours. The mixture is cooled to room temperature and filtered. The filtrate is examined by gas chromatography and is found to contain 0.52 g (40 percent yield) of 1-cyanobenzocyclobutene.

C. Preparation of 5-Amino-1-Cyanobenzocyclobutene

The 1-cyanobenzocyclobutene is added slowly to a cold solution of sodium nitrate in cold sulfuric acid. The so-formed nitro compound is isolated, dissolved in ethanol, and reduced by hydrogenation over a palladium on carbon catalyst.

D. Preparation of 1,2-Diiodobenzocyclobutene

In a 12-liter, three-neck flask equipped with two reflux condensers and an air-driven stirrer, is placed 6.5 liters of absolute ethanol. The system is connected to a nitrogen line and bubbler through a three-way valve. The system is purged with nitrogen and 437.5 g (1.037 moles) of α,α,α',α'-tetrabromo-o-xylene and 1,948.1 g (12.98 moles) of sodium iodide are added with stirring. The reaction mixture is stirred and heated under reflux for 10 days under nitrogen. The mixture is cooled and the ethanol solvent removed with a rotary evaporator. The residue is stirred with methylene chloride and filtered. The filtrate is extracted with water and then stirred for 15 minutes with a 20 percent sodium sulfite solution. The methylene chloride layer is separated and extracted 4 times with water. It is then dried over magnesium sulfate and filtered. The methylene chloride is then removed on a rotary evaporator and the residue is treated with hot methanol. The insoluble tarry impurities are separated by decantation and the methanol solution is treated with activated charcoal. The methanol-charcoal mixture is boiled for 15 minutes and then filtered through celite to remove the charcoal. The charcoal treatment procedure is then repeated 4 more times. Following this, the methanol filtrate is placed in a round-bottom flask and the methanol is removed on a rotary evaporator to give the crude product as a beige solid. This is recrystallized from methanol to give 166.9 g of pure product. The filtrate from the recrystallization is evaporated to give an orange oil which, on treatment with methanol, yielded another 62.9 g of pure product. Total yield is 233.8 g or 63.3 percent.

E. Bromination of benzocyclobutene

The brominating agent used in this case is pyridinium hydrobromide perbromide ($C_5H_5N^{\oplus}HBr_3^{\ominus}$, formula weight 319.86). This reagent is prepared just prior to its use via the method of Fieser, *Reagents for Organic Synthesis,* Fieser & Fieser, pp. 967–982.

A 2000-ml round-bottom, three-neck flask is equipped with a reflux condenser connected to a nitrogen line with T and mineral oil bubbler, mechanical stirrer, and a thermocouple attached to a temperature controller. The flask is then charged with 4.5 g of mercuric acetate ($Hg(O_2CCH_3)_2$, f.w. 318.68, 14.12 mmoles), 28.5 g of benzocyclobutene ($C_8H_8$, m.w.=104.15, 0.274 mole), and 950 ml of glacial acetic acid. This mixture is stirred, 60 g of pyridinium hydrobromide perbromide is added, and the reaction is heated to 50° C. After 4 hours, another 60 g of brominating agent is added. The mixture is sampled and the conversion of starting material to product is monitored by gas chromatography. The addition of 60-g increments of brominating agent proceeds in this manner until conversion is complete (4 days, 460 g of pyridinium hydrobromide perbromide total).

The reaction product is isolated by first decanting the acetic acid solution into a separatory funnel and diluting with 500 ml of water. The crystals of pyridinium hydrobromide perbromide are then soaked in methylene chloride (250 ml) to leach out any residual product. This methylene chloride solution is decanted into the separatory funnel, the funnel shaken, and the layers separated. The aqueous solution is returned to the funnel and the process is repeated twice more. The methylene chloride extracts are combined and washed with 500 ml of $Na_2SO_3$ (5 percent), 500 ml of water, 500 ml of aqueous hydrochloric acid (10 percent), 500 ml of water, 500 ml of $NaHCO_3$ (saturated), 500 ml of water, and dried over $MgSO_4$. The methylene chloride is then carefully removed via distillation, and the product is isolated by vacuum distillation using a column packed with stainless steel mesh. Bromobenzocyclobutene is collected at 58° C.–60° C. with a vacuum of 1.5 mm Hg. Total of 32.8 g is isolated pure, and the pot residue contains another 8–10 g of material. Isolated yield is 65.6 percent of theoretical value.

F. Carbonylation of Bromobenzocyclobutene to Prepare Carbomethoxybenzocyclobutene This reaction is run in a 450-ml Parr pressure reactor fitted with a magnetically coupled stirring system. Into this reactor is entered 30 g of bromobenzocyclobutene (0.164 mole), 16.5 g of $(CH_3CH_2)_3N$ (0.164 mole, freshly distilled over Na metal), 100 ml of $CH_3OH$ (Burdick & Jackson brand), and the catalyst mixture of 1.1 g of $Pd(O_2CCH_3)_2$ (4.9 mmoles, 3 mole percent) and 1.1 g of $PPh_3$ (recrystallized from ethanol). The reactor is then sealed and attached to a CO cylinder. The mixture is purged with 600 psig CO three times while stirring, and finally pressurized and held at 600 psig CO. The temperature is raised to 125° C., and held under these conditions overnight (approximately 16 hours). After this time, the unreacted CO is vented, and the reaction vessel is cooled to ambient temperature. The methanol solution is diluted with 200 ml of water, and the product extracted with 3×150 ml of $CH_2Cl_2$. The methylene chloride solution is then washed with 250 ml of water, 250 ml of HCl (5 percent), 250 ml of water, 250 ml of $NaHCO_3$ (saturated), 250 ml of water, and dried over $MgSO_4$. The methylene chloride solution is checked for conversion by gas chromatographic analysis, and the composition is discovered to be 97 percent 4-carbomethoxybenzocyclobutene. The solvent is then removed by distillation, and the product is then purified by vacuum distillation at 66° C.–67° C., 1 mm Hg vacuum.

G. Preparation of Benzocyclobutene 4-Carboxylic Acid by Hydrolysis of 4-Carbomethoxybenzocyclobutene A 500-ml round-bottom, single-neck flask is equipped with magnetic stirrer and reflux condenser attached to a nitrogen line with T mineral oil bubbler. To this flask is added 10 g of 4-carbomethoxybenzocyclobutene (m.w. 162.19 g, 0.062 mole) and 190 ml of methyl alcohol (Burdick & Jackson brand). This solution is stirred, and to it is added 60 ml of aqueous NaOH solution containing 7.5 g of NaOH (m.w. 39.998, 0.188 moles). This mixture is stirred at room temperature for one hour, after which the solution is transferred into a 1000-ml separatory funnel. The strongly alkaline solution is first diluted with 250 ml of water, and washed with 250 ml of $CH_2Cl_2$. The aqueous solution is then drained into a large beaker and acidified with concentrated HCl until the solution is strongly acidic. The acid, which forms a white precipitate upon acidification, is then collected with 3×250 ml of $CH_2Cl_2$. The methylene chloride solution is dried over $MgSO_4$ and the solvent removed via rotary evaporation. The carboxylic acid (8.95 g) is recovered as a white solid (98 percent of theoretical yield).

H. Preparation of Benzocyclobutene Acid Chloride and Reaction Thereof With a Diamine 4-Carbomethoxybenzocyclobutene (29.2 g) is hydrolyzed to benzocyclobutene-4-carboxylic acid using the procedure given under Preparation (G). The acid is dried and added to 50 ml of freshly distilled thionyl chloride in a 500-ml single-neck flask equipped with a reflux condenser, nitrogen blanket and magnetic stirrer. The mixture is refluxed under nitrogen for ½ hour. The excess thionyl chloride is removed with a vacuum pump leaving the so produced acid chloride as a brown oil. The product weighs 28.6 g and is used without further purification. The acid chloride is dissolved in 100 ml of methylene chloride and added to a 2-liter three-neck flask equipped with a thermometer port (the 2-liter flask and accessories are dried with a heat gun prior to adding the acid chloride). The flask is then equipped with a reflux condenser topped with a nitrogen line and mineral oil bubbler, an addition funnel fitted with a septum and a thermocouple probe placed in the thermometer port. Triethylamine (20 g) is then added to the flask. Heptamethylene diamine (10.6 g) is weighed out into a bottle in a dry box and the bottle capped with a septum. The diamine is diluted with 100 ml of methylene chloride and transferred via a syringe to the addition funnel. The diamine solution is then added dropwise to the reaction mixture. After this addition, the addition funnel is filled with methylene chloride and this is also added to the reaction mixture. This rinsing procedure is then repeated a second time. Finally, the reaction mixture is heated at reflux for 16 hours. The mixture is cooled to room temperature and poured into a separatory funnel. The mixture is then washed successively with 500 ml of water, 500 ml of 5 percent hydrochloric acid, 500 ml of water, 500 ml of saturated sodium bicarbonate and finally dried over anhydrous magnesium sulfate. The methylene chloride is evaporated off to give the product as a light brown solid. This is diluted with 250 ml of toluene and heated. The solution is then filtered (after cooling for 15 minutes) and the solid removed through this filtration is again dissolved in 250 ml of toluene. This solution is also heated, cooled for 15 minutes and filtered (suction). The solid removed by this filtration shows no coloration upon dilution with toluene so the solid is removed by suction filtration and dried in vacuo. The final weight of the product is 24.58 g resulting in a 77.2 percent yield based on the amount of diamine added.

I. Preparation of a Bis-Benzocyclobutene Monomer Derived From a 1,n+2-Alkyldiacid

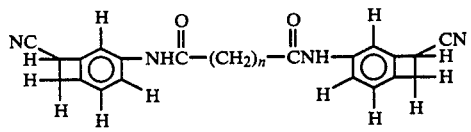

wherein n is the number of carbons between the carboxyl groups.

(a) n=2

5-Amino-1-cyanobenzocyclobutene (hereinafter called Compound A) (12.58 g, 0.089 mole) and triethylamine (7.05 g, 0.07 mole) are dissolved in 300 ml of methylene chloride. The solution is cooled to 0° C. in an ice bath, with stirring unger argon. A solution of 6.91 g (0.045 mole) of succinyl chloride in 100 ml of methylene chloride is added dropwise to the cooled solution. The reaction mixture is stirred for 30 minutes at 0° C. after the addition is complete. The reaction mixture is then warmed to room temperature and is poured into 400 ml of water. The mixture is extracted 3 times with 250-ml portions of methylene chloride. The combined methylene chloride extracts are washed once with 400 ml of a 5 percent hydrochloric acid solution. The methylene chloride layer is washed with 400 ml of water. Next, the methylene chloride solution is washed with 400 ml of saturated sodium bicarbonate and finally with 400 ml of water. The methylene chloride is removed under vacuum to give the product as a gray solid. Yield is 10 g or 60.6 percent.

(b) n=3

This monomer is prepared as under (a) using different amounts of reactants and is run in a nitrogen atmosphere. Compound A (12.13 g, 0.086 mole) and triethylamine (8.7 g, 0.086 mole) are dissolved in 300 ml of methylene chloride. Glutaryl chloride (6.61 g, 0.038 mole) is dissolved in 100 ml of methylene chloride and is added dropwise to the reaction mixture. The reaction is run and worked up the same as under (a) except that the methylene chloride solution is dried over anhydrous magnesium sulfate, filtered and then concentrated under vacuum. The product is a green solid. The yield is 13 g, 86.6 percent.

(c) n=4

This monomer is prepared in the same manner as described in (a) using different amounts of reactants and is run in a nitrogen atmosphere. Compound A (11.7 g, 0.083 mole) and triethylamine (8.4 g, 0.083 mole) are dissolved in 300 ml of methylene chloride. Adipoyl chloride (6.90 g, 0.038 mole) is dissolved in 100 ml of methylene chloride and is added dropwise to the mixture. The workup of the reaction mixture is the same as under (b), obtaining 14.7 g (98 percent) of a white solid.

The product is recrystallized from ethanol to give 8 g (53.3 percent yield) of solid.

(d) n=5

Thionyl chloride (5.12 g, 0.043 mole) is added dropwise under nitrogen to 20 ml of dry N,N-dimethylformamide which is cooled and stirred for 30 minutes at 0° C. in an ice bath. Pimelic acid (3.20 g, 0.020 mole) is dissolved in 15 ml of dry N,N-dimethylformamide and is added dropwise to the cooled reaction mixture. The reaction mixture is stirred an additional 30 minutes and then is warmed to room temperature and is stirred another 30 minutes, then again is cooled to 0° C. in an ice bath. Compound A (6.77 g, 0.047 mole) and triethylamine (6.06 g, 0.060 mole) are dissolved in 20 ml of dry N,N-dimethylformamide. This solution is then added dropwise to the cooled reaction mixture. The reaction mixture is slowly warmed to room temperature overnight. The reaction mixture is poured into 500 ml of water and is stirred for 30 minutes. Next, the water layer is extracted then washed twice with 200-ml portions of chloroform. The chloroform washes are combined and washed once with 300 ml of a saturated sodium bicarbonate solution, and once with 300 ml of water. The chloroform solution is washed once with 300 ml of a 10 percent hydrochloric acid solution and finally with 300 ml of water. The chloroform solution is then dried over anhydrous magnesium sulfate, filtered and concentrated under vacuum. The product obtained is column chromatographed over silica gel using ethyl acetate as the eluting solvent. A yellow colored solid is obtained.

(e) n=6

This monomer is prepared by the same procedure that is used under (d) except that 0.02 mole suberic acid was employed, and 0.048 mole of Compound A and 0.061 mole of triethylamine are dissolved in 15 ml of N,N-dimethylformamide and are added to the cooled reaction mixture. A white solid is obtained.

(f) n=7

This monomer is prepared by the method used under (d). Thionyl chloride (4.53 g, 0.038 mole) is added while stirring to 20 ml of dry N,N-dimethylformamide. Azelaic acid (3.33 g, 0.018 mole) is dissolved in 15 ml of N,N-dimethylformamide and is added to the reaction mixture at 0° C. The reaction mixture is then stirred as indicated previously under (d). Compound A (6.0 g, 0.043 mole) and triethylamine (5.37 g, 0.053 mole) are dissolved in 15 ml of N,N-dimethylformamide and added dropwise to the cooled reaction which is worked up as in (d), obtaining a brown solid.

(g) n=8

This preparation involves dissolving Compound A (1.41 g, 0.01 mole) and pyridine (1.0 g, 0.013 mole) in 35 ml of methylene chloride. This solution is cooled to 0° C. in an ice bath with stirring under nitrogen. Sebacoyl chloride (1.20 g, 0.005 mole) is dissolved in 15 ml of methylene chloride and is added dropwise to the cooled solution. The reaction mixture is stirred for 30 minutes at 0° C. and is warmed to room temperature. The reaction mixture is poured into 100 ml of water and is extracted 3 times with 50-ml portions of methylene chloride. The methylene chloride extracts are combined and washed once with 100 ml of a 5 percent hydrochloric acid solution. The methylene chloride solution is then washed with 100 ml of water and is dried over anhydrous magnesium sulfate. The solution is filtered and concentrated under vacuum to obtain a white-colored solid. The solid product is dried under a vacuum overnight.

J. Preparation of Bisbenzocyclobutene Monomer Containing a Diamido Bridging Member

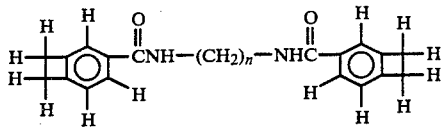

The general reaction sequence is to react compound (G), benzocyclobutene 4-carboxylic acid with 1,1-carbonyl diimidazole to give an imidazole derivative which is further reacted with a polyalkylene diamine to result in the bis-amide monomer.

(a) n=3

1,1-Carbonyldiimidazole (2.64 g, 0.016 mole) is dissolved in 45 ml of dry tetrahydrofuran and stirred under nitrogen at room temperature. The benzocyclobutene 4-carboxylic acid (2.37 g, 0.016 mole) is dissolved in 45 ml of dry tetrahydrofuran and added dropwise to the stirred imidazole solution at room temperature. The mixture is stirred for 30 minutes at room temperature and then heated at reflux overnight. The mixture is then cooled to room temperature and a solution of 1,3-propanediamine (0.53 g, 0.0072 mole) in 25 ml of dry tetrahydrofuran added dropwise. After this addition, the mixture is stirred at room temperature for 1½ hours and then heated to reflux overnight. The mixture is cooled to room temperature and poured into 300 ml of water with stirring. The mixture is extracted with three 200-ml portions of methylene chloride. The methylene chloride extracts are combined and washed with three 400-ml portions of a 10 percent hydrochloric acid solution. Next, the methylene chloride extract is washed with one 500-ml portion of water followed by two washings with 400-ml portions of saturated sodium bicarbonate. Finally, the methylene chloride extract is washed with two 500-ml portions of water and dried over anhydrous magnesium sulfate. The magnesium sulfate is filtered off and the filtrate evaporated to yield 2.5 g of crude product. This is recrystallized from ethanol to yield 1.5 g (0.0045 mole) of pure product. The melting point of the product is 172° C.–178° C.

(b) n=5

The same procedure and workup is used as in the preceding example. The quantities of reactants and product are: benzocyclobutene 4-carboxylic acid (2.22 g, 0.015 mole); 1,1-carbonyldiimidazole (2.38 g, 0.0147 mole); 1,5-pentanediamine (0.72 g, 0.0071 mole); and product weight (1.8 g, 0.0049 mole). The melting point is 181° C.–185° C.

(c) n=6

The same procedure and workup is used as in the procedure where n=3. The quantities of reactants and product are: benzocyclobutene 4-carboxylic acid (2.22 g, 0.015 mole); 1,1-carbonyldiimidazole (2.43 g, 0.015 mole); 1,6-hexanediamine (0.79 g, 0.0068 mole); and product weight (0.65 g, 0.0017 mole). The melting point is 185° C.–194° C.

(d) n=7

The same procedure and workup is used as in the procedure where n=3. The quantities of reactants and product are: benzocyclobutene 4-carboxylic acid (2.22 g, 0.015 mole); 1,1-carbonyldiimidazole (2.48 g, 0.015 mole); 1,7-heptanediamine (0.99 g, 0.0076 mole); and product weight (0.6 g, 0.0015 mole). The melting point is 141° C.–145° C.

(e) n=8

The same procedure and workup is used as for the procedure where n=3. The quantities of reactants and product are: benzocyclobutene 4-carboxylic acid (1.48 g, 0.01 mole); 1,1-carbonyldiimidazole (1.62 g, 0.01 mole); 1,8-octanediamine (0.65 g, 0.0045 mole); and product weight (0.5 g, 0.0012 mole). The melting point is 172° C.–176° C.

K. Formation of a Bisbenzocyclobutene Ester Monomer Derived From Bisphenol-A

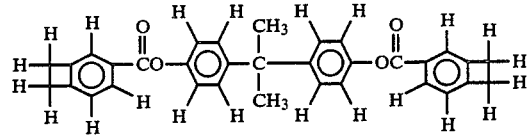

A 2000-ml three-neck, round-bottom flask is equipped with magnetic stirrer, 125-ml addition funnel, reflux condenser with nitrogen blanket, and stopper. To this system is added 25.62 g of 4,4'-isopropylidene diphenol (bisphenol A, m.w. 228.3 g, 0.1122 mole), 24.0 g of $(CH_3CH_2)_3N$ (0.238 mole, m.w. 101 freshly distilled over Na metal), and 600 ml of $CH_2Cl_2$ (Burdick and Jackson brand). This flask is now cooled with an ice water bath to 10° C., with stirring, and 38.78 g of benzocyclobutene 4-acid chloride (m.w. 166.5 g, 0.233 mole) in 75 ml of $CH_2Cl_2$ is entered into the addition funnel. This solution is added dropwise to the stirring bisphenol A solution. When all of the acid chloride solution has been added, the addition funnel is washed with 2×100 ml of $CH_2Cl_2$. The reaction mixture is then allowed to stir overnight. The mixture is then entered into a separatory funnel and washed with 500 ml of water, 500 ml of HCl (5 percent), 500 ml of water, 500 ml of $NaHCO_3$ (saturated), 500 ml of water, and dried over $MgSO_4$. The mixture is then checked by HPLC to determine the relative purity of the monomer produced. The methylene chloride is removed via rotary evaporation and the resultant off-white solid is recrystallized from 600 ml of acetone. The first crop of white crystals is removed from solution via filtration and the solution remaining is concentrated to 250 ml and again recrystallized. The second crop of crystals is also isolated via filtration and the remaining solvent is removed to leave a light brown residue. Final weights and purity (by HPLC) are as follows: first crop, 42.10 g, 99.8 percent; second crop, 6.07 g, 99.3 percent; residue, 6.6 g. Yield is 88 percent of theoretical.

L. Preparation of Bisbenzocyclobutene Monomer Derived From an Olefinic Aromatic Compound Corresponding to the Formula

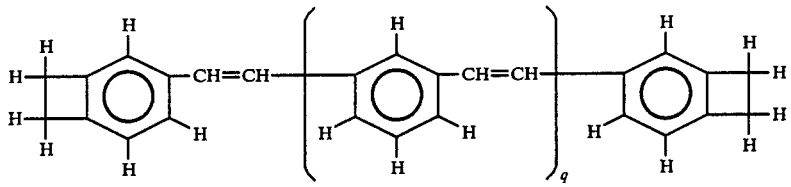

(a) q=3

A 25-ml flask equipped with a reflux condenser, nitrogen inlet, and magnetic stirring bar is charged with m-dibromobenzene (1.0 g, $4.2 \times 10^{-3}$ m), m-divinylbenzene (2.75 g, $2.1 \times 10^{-2}$ m), tri-n-butylamine ($8.4 \times 10^{-3}$ m), tri-o-tolylphosphine (64 mg, $2.1 \times 10^{-4}$ m), palladium (II) acetate (20 mg, $8.4 \times 10^{-5}$ m), and acetonitrile (10 ml). The mixture is stirred under nitrogen and heated to reflux for 2 hours. The grey slurry is cooled to room temperature and stirred into 60 ml of 10 percent hydrogen chloride. The resulting precipitate is collected by filtration, washed with water, and air dried. This product is dissolved in ethylacetate, filtered, and the solvent evaporated to yield a yellow residue. Recrystallization of the residue from heptane gives 0.60 g (42 percent yield) of a compound of the formula

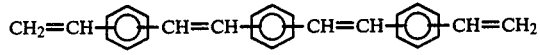

hereinafter referred to as determinal olefin, with a melting point of 105° C.

A 25-ml flask eqipped with a reflux condenser, nitrogen inlet and magnetic stirring bar is charged with 4-bromobenzocyclobutene (1.5 g, $8 \times 10^{-3}$ moles), the determinal olefin from part A (1.34 g, $4 \times 10^{-3}$ moles), tri-n-butylamine (1.8 g, $9.7 \times 10^{-3}$ moles), tri-o-tolylphosphine (62 mg, $4.0 \times 10^{-4}$ moles), palladium II acetate (18 mg, $8.0 \times 10^{-5}$ moles) and acetonitrile (5 ml). The reaction mixture is heated to reflux under nitrogen for 4 hours. The mixture is cooled to room temperature and stirred into 60 ml of 10 percent hydrochloric acid. The precipitate is collected by filtration, washed with water and air dried. The dried precipitate is then dissolved in 150 ml of boiling toluene, filtered hot and cooled to yield 310 ml of the product g=3. The monomer has a melting point of 180° C.-215° C.

(b) q=1

A 25-ml flask equipped with a reflux condenser, nitrogen inlet, and magnetic stirring bar is charged with 4-bromobenzocyclobutene (1.50 g, $8.0 \times 10^{-3}$ m), m-divinylbenzene ($4.0 \times 10^{-3}$ m), tri-n-butylamine (1.8 g, $9.7 \times 10^{-3}$ m), tri-o-tolylphosphine (62 mg, $4.0 \times 10^{-4}$ m), palladium (II) acetate (18 mg, $8.0 \times 10^{-5}$ m), and acetonitrile (5 ml). The reaction mixture is heated to reflux under nitrogen with stirring for 4 hours. The solidified mixture is cooled to room temperature and stirred into 60 ml of 10 percent hydrogen chloride. The resulting precipitate is collected by filtration, washed with water, and air dried.

The precipitate is dissolved in 75 ml of boiling ethylacetate, filtered hot, and cooled to yield 800 mg (60 percent) of the desired monomer with a melting point of 150° C.-152° C.

EXAMPLE 1

Partially Polymerized Composition From a Bisbenzocyclobutene Monomer Derived From 1,7-Heptanedicarboxylic Acid

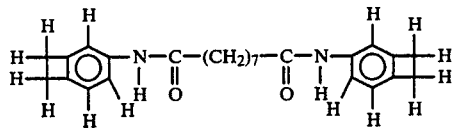

The monomer is prepared by reacting 4-aminobenzocyclobutene with 1,7-heptanedicarboxylic acid in the presence of tetrahydrofuran. About 10 g of N,N'-carbonydiimidazole in 150 ml of tetrahydrofuran is added to a flask equipped with magnetic stirrer, condenser, and two dropping funnels. A solution of 1,7-heptanedicarboxylic acid in tetrahydrofuran is provided by mixing about 6 g of the acid with 90 ml of the tetrahydrofuran. The solution is added dropwise to the carbonydiimidazole/tetrahydrofuran mixture, stirred for an hour and then heated to 60° C. for about 2.5 hours. The mixture is cooled to 25° C., and 7.4 g of 4-aminobenzocyclobutene in 70 ml of tetrahydrofuran solution is added dropwise. The mixture is heated at 60° C. for 6 hours and then allowed to stand at room temperature overnight. The product is poured into water, giving a white precipitate which is extracted into methylene chloride. The organic solution is then washed with acid, water, base, water and the solvent is removed under vacuum. The product is dried at 70° to 80° C. under 1 to 2 mmHg for about 4 hours. The product is recrystallized from absolute ethanol and is found to have a melting point of 163° to 165° C.

(i) Preparation of Partially Polymerized Composition

To a reaction vessel 0.75 g of the monomer is added. The monomer is heated for 8 minutes at 200° C. The monomer is very fluid. The temperature is raised to 220° C. for 11 minutes, and the monomer exhibits a slow viscous flow. The viscosity is substantially greater than the melted monomer's initial viscosity. The partially polymerized composition is removed from the heat and cooled to a pale yellow glassy solid.

(ii) Preparation of a Cured Polymer in a Compression Molding Process

The partially polymerized composition is ground to a fine powder. The powdered partially polymerized composition is placed in a small compression mold which is treated with Fluorad ® Brand Surface Modifier FC-723. The mold is heated to 200° C. and slight pressure is applied to compact the partially polymerized composition. The mold temperature is increased to 250° C. and after 10 minutes, 15,000 pounds per square inch are applied. The pressure and temperature are maintained for 1.5 hours and the temperature is then lowered while the mold is cooled under pressure. A pellet of a cured polymeric composition is provided which is free of voids and cracks, has smooth surfaces and is light yellow in color.

EXAMPLE 2

Partially Polymerized Compositions From the Compound of Preparation of J (d), the Bisbenzocyclobutene Monomer Derived From 1,7-Heptanediamine

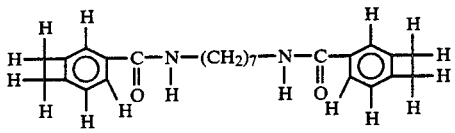

(i) Preparation of Partially Polymerized Composition

An 8.2 g sample of the monomer is provided to a reaction vessel. The monomer is heated in a nitrogen atmosphere under agitation at 200° C. for 10 minutes, then at 220° C. for 16 minutes, and a thick viscous syrup is provided. The viscosity is substantially greater than the initial viscosity of the melted monomer. The partially polymerized composition is cooled, and forms a solid part which is broken into small pieces.

(ii) Preparation of Cured Polymeric Composition in a Compression Molding Process A 6.2 g sample of the partially polymerized composition is placed in a chromed, stainless steel mold, and 2 tons pressure is applied. The mold is heated to 200° C. and the pressure is raised to 30 tons. The mold is then heated to 240° C. and maintained at that temperature for 1 hours. A solid bar of cured polymeric composition is obtained which has no cracks or voids, although some gel-like regions are observed under 50× magnification. The bar has a tensile modulus of $3.8 \times 10^5$ psi, a tensile strength of 3,800 psi, a density of 1.16 g per cm$^3$, a hardness of 90 (shore d) and 5 percent elongation at break. The coefficient of thermal expansion from 20° to 200° C. is $4.9 \times 10^{-5}$. The water pickup is about 3 weight percent at 100° C.

EXAMPLE 3

Partially Polymerized Composition From a Compound of Preparation K, the Bisbenzocyclobutene Monomer Derived From Bisphenol-A

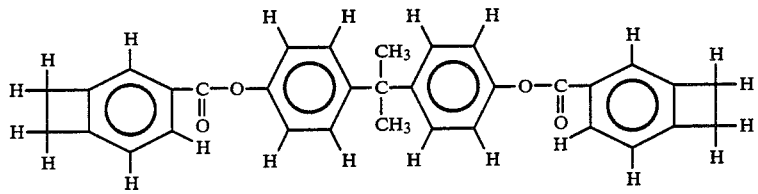

(i) Preparation of Partially Polymerized Composition

A 1.0 g sample of the monomer is placed in a vessel and heated at 212° C. for 49 minutes in a rheometrics study. A partially polymerized composition has a viscosity of 1,678 poise at 212° C. The partially polymerized composition is cooled to room temperature and is a brittle solid. The partially polymerized composition contains about 51 percent unreacted polymerizable functionality as determined by differential scanning calorimetry.

(ii) Preparation of Cured Polymeric Composition in Compression Molding Process

A 0.5 g sample of the partially polymerized composition is ground into small pieces and placed in a compression mold. The mold is heated to 220° C. and 2,000 lbs of pressure is applied. The partially polymerized composition softens and is pliable at about 180° C. The mold temperature is increased to 250° C., the pressure is increased to 4,000 lb pressure and held there for 1 hour. The mold is then cooled under pressure, and a solid part of cured polymeric composition, 0.5 inches in diameter and 0.1 inches thick, is provided. The part has good clarity and is free of visible defects.

(iii) Preparation of Cured Polymeric Composition and Use to Draw Fibers

A 1 g sample of the bisbenzocyclobutene derived from bisphenol-A is heated at 219° C. for 22 minutes. A partially polymerized composition with a viscosity of 115 poise at 219° C. is provided. The partially polymerized composition is a brittle glass-like solid at room temperature.

The partially polymerized composition is heated, softens at 120° C. and melts to a viscous fluid at 160° to 180° C. The heated partially polymerized composition adheres to a glass rod and is drawn to a long thin flexible fiber. The 1 g sample is drawn to a length of 27 inches and is 10 to 20 microns in diameter as measured against 8 micron diameter carbon fibers. The partially polymerized composition in the form of drawn fiber is then heated to 220° C. for 1 hour to provide a cured polymeric composition.

EXAMPLE 4

Partially Polymerized Composition From a Compound of Preparation L, the Bisbenzocyclobutene Derived From Meta-Divinyl Benzene

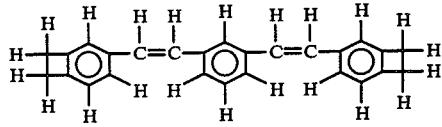

(i) Preparation of Partially Polymerized Composition

A 1 g sample of the monomer is heated from 189° to 222° C. at the rate of 1° C. per minute. The partially polymerized composition has a viscosity of 249 poise at 220° C., the partially polymerized composition is solid at room temperature and becomes gel-like at 180° to 190° C. The partially polymerized composition contains 51 percent unreacted polymerizable functionality as determined by differential scanning calorimetry.

(ii) Preparation of Cured Polymeric Composition in Compression Molding Process

A 0.6 g sample of the partially polymerized composition prepared in D(i) is placed in a compression mold. The mold is heated to 215° to 220° C. and 2,000 lbs of pressure is applied. The mold temperature is increased to 250° C., the pressure is increased to 4,000 lbs. of pressure and is held there for 1 hour. The mold is cooled under pressure and a solid piece is prepared which is 0.5 inch in diameter and 0.1 inch thick. The pellet has good clarity and is free of visible defects.

(iii) Cured Polymeric Composition Coatings (a) Neat Coating

A 0.26 sample of the monomer is heated in an oil bath for 10 minutes at 215° C. under a nitrogen atmosphere. The partially polymerized composition is a brittle solid at room temperature, softens at 100° to 110° C., and is a viscous fluid at 150° to 160° C. NMR data indicate that about 67 percent of the benzocyclobutene sites are unreacted.

A 60 mg sample of the partially polymerized composition is melted on a copper plate at 120° C. and is spread to form a viscous liquid film. The plate and sample are heated under a nitrogen atmosphere for 30 minutes at 200° C. and then for 1 hour at 250° C. A hard 0.5 inch by 1.4 inch by 0.003 inch thick coating is provided.

(b) Cured Polymeric Composition Solvent Coating

A 25 percent solution of the partially polymerized composition in toluene is spread on a copper plate and heated slowly from 70° to 160° C. The sample is further heated at 200° C. for 30 minutes, then at 250° C. for 1 hour. A hard 0.5 inch by 0.4 inch by 0.007 inch thick coating is provided.

EXAMPLE 5

Partially Polymerized Composition from 1,2-Bis-(4-Benzocyclobutenyl)ethane Monomer

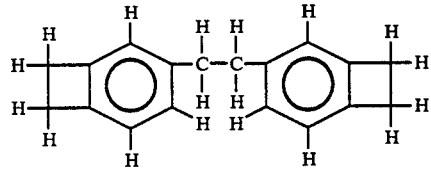

(i) Preparation of 1,2-Bis-(4-benzocyclobutenyl)ethane

The monomer is prepared by heating a mixture of 4-bromobenzocyclobutene with 4-vinylbenzocyclobutene at reflux. Vinylbenzocyclobutene is prepared by adding 0.98 g of 4-bromobenzocyclobutene, 0.04 g palladium (II) acetate, and 0.17 g of tri-o-tolylphosphine to a mixture of 100 ml acetonitrile and 0.6 g of triethylamine in a 450 ml Parr pressure reactor. The reactor is pressurized with 250 psig ethylene. The mixture is heated to 125° C. and stirred for 16 hours. The apparatus is cooled and the remaining ethylene is vented. The product is washed with water and 5 percent hydrochloric acid and dried over MgSO₄. The solvent is removed to provide 4-vinylbenzocyclobutene. A 2.4 g sample of 4-bromobenzocyclobutene, 1.7 g of 4-vinylbenzocyclobutene, 2.4 g of tri-n-butylamine, 100 mg of tri-o-tolylphosphine, 29 mg palladium (II) acetate and 10 ml acetonitrile are added to a flask equipped with a reflux condenser, nitrogen inlet, and magnetic stirrer. The reaction mixture is heated to reflux under nitrogen for 4 hours. The solution is cooled to room temperature and stirred into 60 ml of 10 percent hydrochloric acid solution. The precipitate is collected by filtration, washed with water and air dried. The product is recrystallized from ethylacetate and has a melting point of 132° to 133° C.

The product is hydrogenated in the presence of a palladium on carbon catalyst. A Parr hydrogenator bottle is charged with 660 mg of the 1,2-(bisbenzocyclobutenyl)ethene product prepared above, 100 ml ethyl acetate, 60 mg of 5 percent palladium on carbon and 50 psi hydrogen. The catalyst is removed by filtration after 60 minutes and the solvent evaporated. The white residue is recrystallized from heptane, and the 1,2-bis(benzocyclobutenyl)ethane with a melting point of 86° to 87° C. is provided.

(ii) Partially Polymerized Composition

A 1.0 g sample of the monomer is heated to 210° to 220° C. for 20 minutes. The partially polymerized composition, after cooling to room temperature, is a pale yellow glassy solid.

(iii) Preparation of Cured Polymeric Composition

A 20 percent solution of the partially polymerized composition in methylene chloride is cast onto glass and aluminum plates. After the solvent evaporates, the coated plates are heated to 250° C. under nitrogen atmosphere. After 60 minutes at 250° C., the samples are cooled to room temperature. The coatings are approximately 0.002 inch thick, are clear, light yellow and holds tenaciously to the plates.

EXAMPLE 6

Partially Polymerized Composition From 1-(2-Napthyl)-2-(4-benzocyclobutenyl)ethene

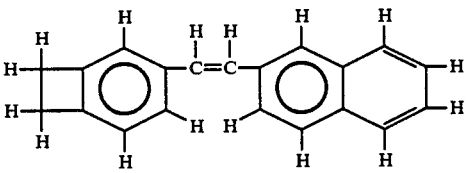

(i) Preparation of 1-(2-Napthyl)-2-(4-Benzocyclobutenyl)ethene

The monomer is prepared by reacting 2-vinylnaphthalene with 4-bromobenzocyclobutene in the presence of a palladium catalyst.

(ii) Preparation of Partially Polymerized Composition

A 1 g sample of the monomer is heated at a rate of 1 degree per minute from 190° C. to 235° C. to provide a 100 poise liquid. The sample is cooled to room temperature and is a glassy solid. Proton NMR spectroscopy shows that about 60 percent of the benzocyclobutene sites remain unreacted. Size exclusion chromatography show a mixture of polymer and monomer, wherein the polymer has molecular weights of as high as 10,000.

(iii) Cured Polymeric Compositions Used as a Solvent Cast Coating

A 20 weight percent solution of the partially polymerized composition in toluene is cast onto a copper plate. The coated plate is heated to 100° C. to evaporate the solvent, and the temperature is raised to 250° C. The polymer film is clear and yellow.

(iv) Cured Polymeric Compositions Used as a Neat Coating

A 50 mg sample of the partially polymerized composition is melted and coated onto a copper plate at 200° C. The temperature is raised to 250° C. for 1 hour to form a clear, yellow polymer film.

(v) Cured Polymeric Compositions in a Compression Molding Process

A 0.5 g sample of the partially polymerized composition is placed in a compression mold treated with 3M FC-723 Fluorad ® mold release. The mold is heated to 170° C. and 2,000 pounds of force is applied. The sample is heated to 200° C. for 10 minutes, then the temperature is increased to 220° C. for 10 minutes and the pressure is then increased to 10,000 pounds. The mold is heated to 250° C. for 1 hour, and then is cooled to room temperature at which point the pressure is released. The polymeric composition is in the form of a solid, clear, yellow part.

EXAMPLE 7

Partially Polymerized Composition From 1-(Phenyl)-2-(4-Benzocyclobutenyl)ethene

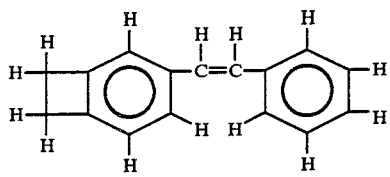

(i) Preparation of 1-Phenyl-2-(4-Benzocyclobutenyl)ethene

The monomer is prepared by reacting styrene with 4-bromobenzocyclobutene in the presence of a palladium catalyst.

(ii) Preparation of Partially Polymerized Composition

A 1 g sample of the monomer is heated at 200° C. for 30 minutes, and then 220° C. for 45 minutes. The sample is cooled to room temperature, and is a glassy solid. Proton NMR spectroscopy shows that 60 percent of the benzocyclobutene sites remain unreacted. Size exclusion chromatography shows a mixture of monomer and polymers having molecular weights of as high as 10,000. Differential Scanning Calorimetry shows no melting endotherm and a polymerization exotherm centered near 250° C.

EXAMPLE 8

Partially Polymerized Compositions Prepared From Precipitation Process of a Compound of Preparation (J)
(d) a Bisbenzocyclobutene Monomer Derived From 1,7-Heptanediamine

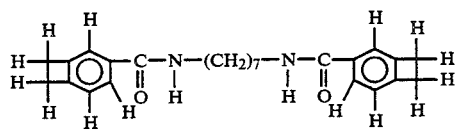

A 50 g sample of biphenyl is added to a flask equipped with a reflux condenser, and a thermocouple well. The biphenyl is heated under nitrogen to 100° C. while stirring. When the biphenyl has melted, a 2 g sample of the bis-benzocyclobutene monomer is added. The mixture is stirred at 100° C. until the monomer sample is dissolved providing a clear solution. The temperature is then raised to 200° C. At about 185° to 190° C. the clear solution becomes cloudy as the partially polymerized composition begins to precipitate. The monomer polymerizes rapidly as the temperature reaches 230° C. The temperature is maintained for 5.5 hours. The mixture is cooled to room temperature, and the mixture forms a solid mass. The solid is heated to 70° C. to liquify the biphenyl and 50 ml of toluene are added to dissolve the biphenyl. A suspension of the partially polymerized composition which is stable at room temperature is provided. The suspension is treated with 400 ml of toluene. The mixture is heated to boiling and filtered while hot. The filtered mass is heated with 200 ml of toluene, cooled to room temperature and filtered. The filtered mass is mixed with toluene, heated to boiling and filtered while hot. The filtered mass is heated to boiling with toluene, cooled to room temperature and filtered. A solid partially polymerized composition product is provided, which is dried in a vacuum oven at 85° C. for 5.5 hours to provide 1.98 g (99 percent of theoretical yield) of product. The product is insoluble in toluene, and does not exhibit a definite melting point by differential scanning calorimetry.

B. Preparation of Cured Polymeric Composition in a Compression Molding Process

A 0.5 g sample of the partially polymerized of A above is placed in a mold treated with 3M FC-723 FLuorad ® mold release. About 7.5 tons pressure is applied. The mold is heated to 170° C. and the force is increased to 10 tons. The temperature and pressure is maintained for 30 minutes. The temperature is increased to 250° C. and maintained for 2 hours. The mold is slowly cooled to room temperature under constant pressure. A polymeric composition in the form of a solid translucent light amber colored part is provided.

The polymers prepared in this method are amber and translucent. The polymer disc exhibits a 4 percent weight loss at 400° C. in nitrogen. The coefficient of thermal expansion of the polymer is $1 \times 10^{-4}$ inch per inch per °C. from 25° to 125° C.; from 125° to 225° C. $20 \times 10^{-4}$ inch per inch per °C.; and from 225° C. to 300° C. $3 \times 10^{-4}$ inch per inch per °C.

What is claimed is:

1. A process for preparing reactive polymeric compositions from arylcyclobutene monomeric compositions, wherein an arylcyclobutene is an aryl moiety to which one or more cyclobutene rings are fused, said process comprising
   (a) subjecting the monomeric composition to polymerization conditions to provide a partially polymerized composition, and
   (b) removing the partially polymerized composition from said conditions.
2. The process of claim 1, further comprising
   (c) subjecting the partially polymerized composition to polymerization and cure conditions to provide a cured polymeric composition.
3. The process of claim 1, wherein said arylcyclobutene monomeric composition comprises a mono-arylcyclobutene monomer, wherein one arylcyclobutene moiety is bonded to a molecular composition in a manner such that said cyclobutene ring provides addition polymerization sites, which corresponds to the formula:

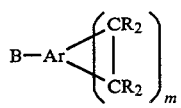

wherein
B is a molecular composition;
Ar is an aryl moiety;
R is separately in each occurrence a hydrogen, or an electron-donating substituent, or an electron-withdrawing substituent; and
m is an integer of one or more.
4. The process of claim 2, wherein said arylcyclobutene monomeric composition comprises a mono-arylcyclobutene monomer wherein one arylcyclobutene moiety is bonded to a molecular composition in a manner such that said cyclobutene ring provides addition polymerization sites,

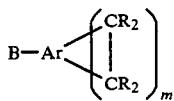

wherein
B is a molecular composition;
Ar is an aryl moiety;
R is separately in each occurrence a hydrogen electron-donating substituent, or an electron-withdrawing substituent; and
m is an integer of one or more.

5. The process of claim 1, wherein said arylcyclobutene monomeric composition comprises a poly(arylcyclobutene)monomer wherein two or more arylcyclobutene moieties connected by a direct bond or a bridging member such that said cyclobutene rings provide addition polymerization sites, wherein said monomer corresponds to the formula

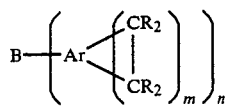

wherein
B is a direct bond or bridging member,
Ar is an aryl moiety;
R is separately in each occurrence a hydrogen, or an electron-donating or an electron-withdrawing substituent;
m is an integer of 1 or more; and
n is an integer of 2 or more.

6. The process of claim 2, wherein said arylcyclobutene monomeric composition comprises a poly(arylcyclobutene)monomer wherein two or more arylcyclobutene moieties are connected by a direct bond or a bridging member such that said cyclobutene rings provide addition polymerization sites,

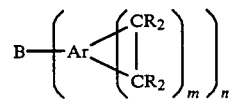

wherein
B is a direct bond or bridging member,
Ar is an aryl moiety;
R is separately in each occurrence a hydrogen, or an electron-donating or an electron-withdrawing substituent;
m is an integer of 1 or more; and
n is an integer of 2 or more.

7. The process of claim 1, wherein step (a) comprises treating arylcyclobutene the monomeric composition at a temperature sufficient to melt said composition to a low viscosity liquid, and to initiate the polymerization of the monomeric composition.

8. The process of claim 7, further comprising the step of (c) subjecting the partially polymerized composition to polymerization and curing conditions to provide a cured polymeric composition.

9. The process of claim 1, wherein step (a) comprises providing said monomeric composition in a liquid which is a solvent for the monomeric composition, and which is a non-solvent for the partially polymerized composition.

10. The process of claim 9, wherein step (a) further comprises treating said monomeric composition at a temperature sufficient to polymerize the arylcyclobutene monomeric composition.

11. The process of claim 10, further comprising the step of (c) subjecting the partially polymerized composition to polymerization and curing conditions to provide a cured polymeric composition.

12. The process of claim 7, wherein said monomeric composition comprises a mono-arylcyclobutene monomer wherein one arylcyclobutene moiety is bonded to a molecular composition in a manner such that said cyclobutene ring provides addition polymerization sites, which corresponds to the formula:

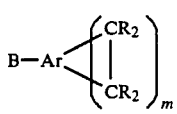

wherein
B is a molecular composition;
Ar is an aryl moiety;
R is separately in each occurrence a hydrogen electron-donating substituent, or an electron-withdrawing substituent; and
m is an integer of one or more.

13. The process of claim 9, wherein said monomeric composition comprises a mono-arylcyclobutene monomer wherein one arylcyclobutene moiety is bonded to a molecular composition in a manner such that said cyclobutene ring provides addition polymerization sites, which corresponds to the formula:

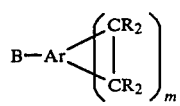

wherein
B is a molecular composition;
Ar is an aryl moiety;
R is separately in each occurrence a hydrogen electron-donating substituent, or an electron-withdrawing substituent; and
m is an integer of one or more.

14. The process of claim 7, wherein the monomeric composition comprises a poly(arylcyclobutene)monomer wherein two or more arylcyclobutene moieties connected by a direct bond or a bridging member such that said cyclobutene rings provide addition polymerization sites, wherein said monomer corresponds to the formula

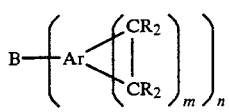

wherein
B is a direct bond or bridging member,
Ar is an aryl moiety;
R is separately in each occurrence a hydrogen, an electron-donating or an electron-withdrawing substituent;
m is an integer of 1 or more; and
n is an integer of 2 or more.

15. The process of claim 9, wherein the monomeric composition comprises a poly(arylcyclobutene)monomer wherein two or more arylcyclobutene moieties connected by a direct bond or a bridging member such that said cyclobutene rings provide addition polymerization sites, wherein said monomer corresponds to the formula

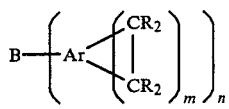

wherein
B is a direct bond or bridging member,
Ar is an aryl moiety;
R is separately in each occurrence a hydrogen, an electron-donating or an electron-withdrawing substituent;
m is an integer of 1 or more; and
n is an integer of 2 or more.

16. The process of claim 12, wherein said mono-arylcyclobutene monomer is 1-(phenyl)-2-(4-benzocyclobutenyl)-ethene which corresponds to the formula

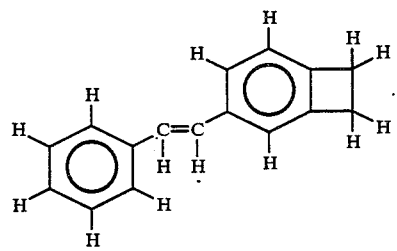

17. The process of claim 12, wherein said mono-arylcyclobutene monomer is 1-(naphthyl)-2-(4-benzocyclobutenyl)-ethene which corresponds to the formula

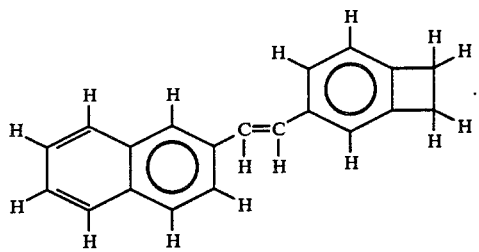

18. The process of claim 13, wherein said mono-arylcyclobutene monomer is 1-(phenyl)-2-(4-benzocyclobutenyl)-ethene which corresponds to the formula

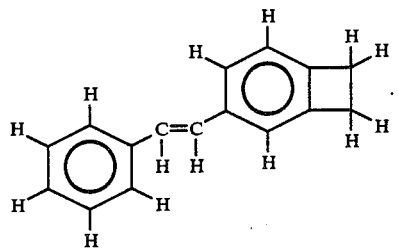

19. The process of claim 13, wherein said mono-arylcyclobutene monomer is 1-(naphthyl)-2-(4-benzocyclobutenyl)-ethene which corresponds to the formula

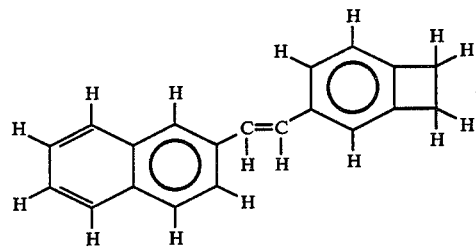

20. The process of claim 14, wherein said poly(arylcyclobutene)monomer is a bisbenzocyclobutene ester monomer which corresponds to the formula

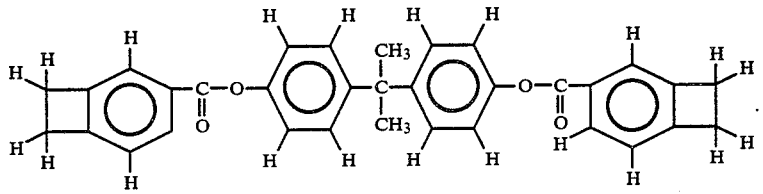

21. The process of claim 14, wherein said poly(arylcyclobutene)monomer is a bis-(4-carbonylbenzocyclobutene)monomer which corresponds to the formula

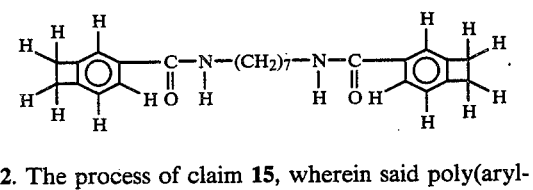

22. The process of claim 15, wherein said poly(arylcyclobutene)monomer is a bis-(4-carbonylbenzocyclobutene)monomer which corresponds to the formula

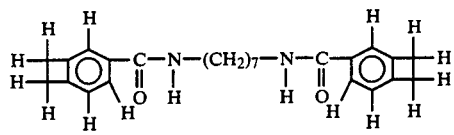

and said liquid is biphenyl.

23. The process of claim 14, wherein said poly(arylcyclobutene)monomer is a bisbenzocyclobutene monomer which corresponds to the formula

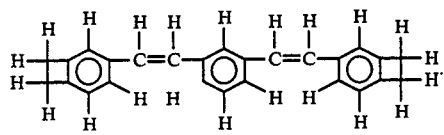

24. The process of claim 14, wherein said poly(arylcyclobutene)monomer is a bisbenzocyclobutene monomer which corresponds to the formula

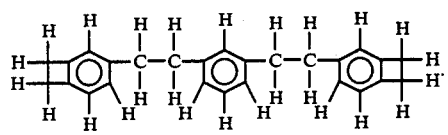

25. The process of claim 14, wherein said poly(arylcyclobutene)monomer is a bisbenzocyclobutene monomer which corresponds to the formula

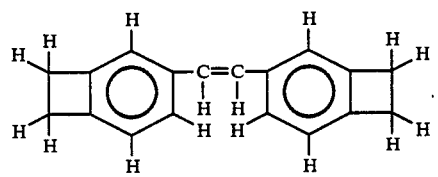

26. The process of claim 14, wherein said poly(arylcyclobutene)monomer is a bisbenzocyclobutene monomer which corresponds to the formula

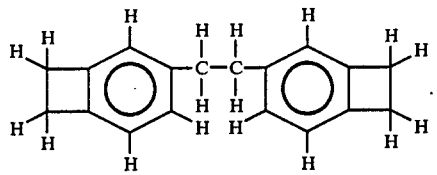

27. The process of claim 14, wherein said poly(arylcyclobutene)monomer is a bisbenzocyclobutene monomer which corresponds to the formula

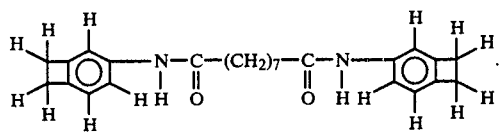

28. The process of claim 12, wherein the mono-arylcyclobutene monomer is a benzocyclobutene which corresponds to the formula

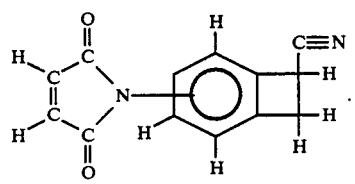

29. The process of claim 16, wherein said arylcyclobutene monomeric composition further comprises the mono-arylcyclobutene monomer 1-(naphthyl)-2-(4-benzo-cyclobutenyl)-ethene, which corresponds to the formula

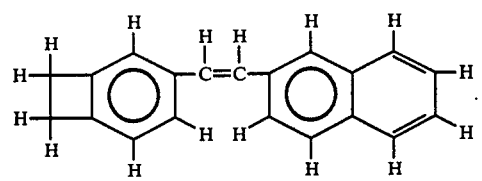

30. The process of claim 16, wherein said arylcyclobutene monomeric composition further comprises a bisbenzocyclobutene ester monomer which corresponds to the formula

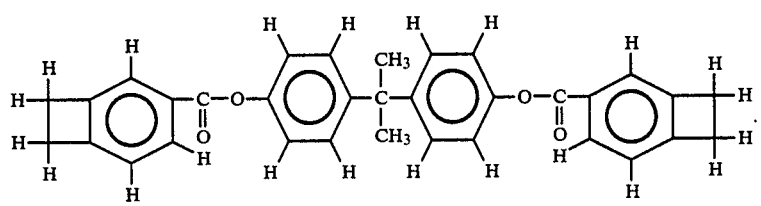

31. The process of claim 17, wherein said arylcyclobutene monomeric composition further comprises a bisbenzocyclobutene ester monomer which corresponds to the formula

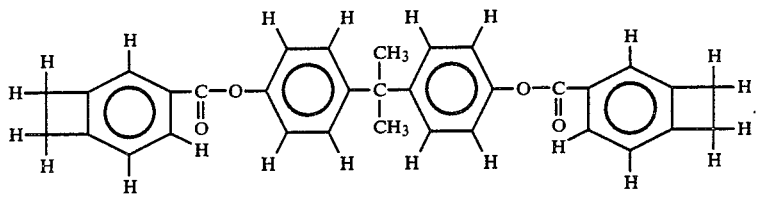

32. The process of claim 16, wherein said arylcyclobutene monomeric composition further comprises a bisbenzocyclobutene monomer which corresponds to the formula

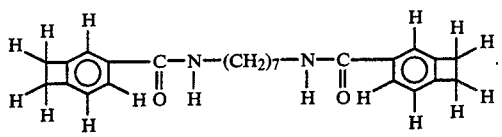

33. The process of claim 17, wherein said arylcyclobutene monomeric composition further comprises a bisbenzocyclobutene monomer which corresponds to the formula

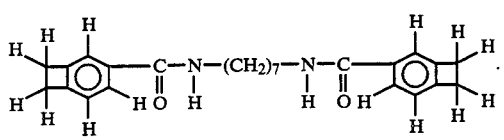

34. The process of claim 21, wherein said arylcyclobutene monomeric composition further comprises an effective amount of an electrical conductive metal composition in the form of a powder.

35. The process of claim 34, wherein said metal composition is gold powder.

36. The process of claim 5, wherein said arylcyclobutene monomeric composition comprises a monomer which contains a moiety which is copolymerizable with said arylcyclobutene moiety.

37. The process of claim 36, wherein said copolymerizable moiety is an ethylenically unsaturated hydrocarbon moiety.

38. The process of claim 36, wherein said copolymerizable moiety is an acetylenic moiety.

39. The process of claim 7, wherein step (d) comprises subjecting said partially polymerized composition to sufficient polymerization temperatures, and sufficient pressure, such that said cured polymeric composition is in the form of a solid piece.

40. The process of claim 39, wherein step (a) comprises subjecting said arylcyclobutene monomeric composition to a temperature of between about 120° C. and about 240° C. for between about 5 to about 60 minutes; and step (d) comprises subjecting said partially polymerized composition to temperatures between about 200° C. and 280° C. for between about 1 to about 5 hours; and to a pressure between about 100 to about 20,000 pounds per square inch.

41. A method for preparing fibers from arylcyclobutene monomeric compositions, wherein an arylcyclobutene moiety is an aryl moiety to which one or more cyclobutene rings are fused, the method comprising
(a) subjecting the monomeric composition to polymerization conditions to provide a partially polymerized composition in the form of a liquid having an effective viscosity,
(b) drawing said viscous liquid into strands, and
(c) subjecting said strands to polymerization and curing conditions.

42. A product of the process of claim 23.

43. The method of claim 36, wherein said copolymerizable monomer is a mono-arylcyclobutene which corresponds to the formula

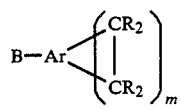

wherein
B is a molecular composition;
Ar is an aryl moiety;
R is separately in each occurrence a hydrogen electron-donating substituent, or an electron-withdrawing substituent; and
m is an integer of one or more.

44. The method of claim 37, wherein said copolymerizable monomer is a mono-arylcyclobutene which corresponds to the formula

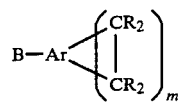

wherein
B is a molecular composition;
Ar is an aryl moiety;
R is separately in each occurrence a hydrogen electron-donating substituent, or an electron-withdrawing substituent; and
m is an integer of one or more.

45. The process of claim 14, wherein said poly(arylcyclobutene)monomer is a bisbenzocyclobutene monomer which corresponds to the formula

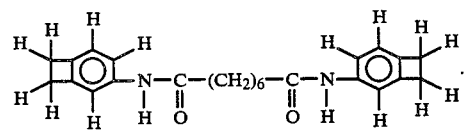

46. The process of claim 14, wherein said poly(arylcyclobutene)monomer is a bisbenzocyclobutene monomer which corresponds to the formula

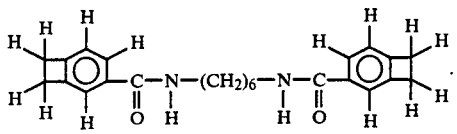

47. The process of claim 2, wherein step (a) comprises mixing said monomeric composition in a solvent which has a boiling point above a temperature at which monomeric composition polymerizes in the presence of an amount of a lithium salt sufficient to solubilize the monomeric composition in the solvent.

48. The process of claim 47, wherein said solvent is a dipolar aprotic solvent with a boiling point above 200° C., and said lithium salt is lithium chloride.

* * * * *